US008093369B2

(12) United States Patent
Shoshan-Barmatz et al.

(10) Patent No.: US 8,093,369 B2
(45) Date of Patent: Jan. 10, 2012

(54) COMPOSITIONS FOR SILENCING THE EXPRESSION OF VDAC1 AND USES THEREOF

(75) Inventors: Varda Shoshan-Barmatz, Omer (IL); Salah Abu-Hamad, Segev Shalom (IL)

(73) Assignee: Ben Gurion University of the Negev Research and Development Authority Ltd., Beer Sheva (IL)

( * ) Notice: Subject to any disclaimer, the term of this patent is extended or adjusted under 35 U.S.C. 154(b) by 0 days.

(21) Appl. No.: 12/088,896

(22) PCT Filed: Oct. 15, 2006

(86) PCT No.: PCT/IL2006/001176
§ 371 (c)(1),
(2), (4) Date: Jun. 3, 2008

(87) PCT Pub. No.: WO2007/043049
PCT Pub. Date: Apr. 19, 2007

(65) Prior Publication Data
US 2008/0267931 A1    Oct. 30, 2008

Related U.S. Application Data

(60) Provisional application No. 60/724,794, filed on Oct. 11, 2005.

(51) Int. Cl.
| C07H 21/04 | (2006.01) |
| C12N 5/00 | (2006.01) |
| C12N 5/02 | (2006.01) |
| C12N 15/11 | (2006.01) |
| C12Q 1/68 | (2006.01) |

(52) U.S. Cl. ............... 536/24.5; 536/23.1; 514/44 A; 435/6.1; 435/325

(58) Field of Classification Search ............ 514/44, 514/218; 536/23.4; 435/6
See application file for complete search history.

(56) References Cited

U.S. PATENT DOCUMENTS

| 4,987,071 A | 1/1991 | Cech |
| 5,436,330 A | 7/1995 | Taira |
| 5,545,729 A | 8/1996 | Goodchild |
| 5,631,115 A | 5/1997 | Ohtsuka |
| 5,780,235 A | 7/1998 | Bandman |
| 6,277,981 B1 | 8/2001 | Tu |
| 6,326,174 B1 | 12/2001 | Joyce |
| 6,506,559 B1 | 1/2003 | Fire et al. |
| 6,841,539 B1 | 1/2005 | Mehta |
| 6,972,171 B1 | 12/2005 | Schlingensiepen |
| 7,022,832 B2 | 4/2006 | Malvy |
| 7,371,404 B2 | 5/2008 | Panzner |
| 7,462,635 B2 | 12/2008 | Sugiyama |
| 2002/0137210 A1 | 9/2002 | Churikov |
| 2003/0157030 A1 | 8/2003 | Davis |
| 2004/0142025 A1 | 7/2004 | MacLachlan |
| 2004/0161777 A1* | 8/2004 | Baker et al. ............ 435/6 |
| 2004/0171003 A1 | 9/2004 | Yoshikawa et al. ........ 435/6 |
| 2005/0100907 A1 | 5/2005 | Kreutzer |
| 2005/0261485 A1 | 11/2005 | Uchida |
| 2006/0078902 A1 | 4/2006 | Bunting |
| 2006/0178324 A1 | 8/2006 | Hadwiger |
| 2006/0204982 A1* | 9/2006 | Morris et al. ............ 435/6 |
| 2006/0211683 A1* | 9/2006 | Selliah et al. ............ 514/218 |
| 2006/0217331 A1 | 9/2006 | Vargeese |

FOREIGN PATENT DOCUMENTS

| WO | 99/49029 A1 | 9/1999 |
| WO | 00/44895 A1 | 8/2000 |
| WO | 01/70949 A1 | 9/2001 |
| WO | 02/055692 A1 | 7/2002 |
| WO | 02/055693 A1 | 7/2002 |
| WO | WO 03/031650 | 4/2003 |
| WO | 2006/060454 A1 | 6/2006 |
| WO | WO 2006/095347 | 9/2006 |

OTHER PUBLICATIONS

"pSUPER.retro.puro : Manual", A vector system for expression of short interfering RNA, 2004, OligoEngine, Inc.*
Zaid et al., The voltage-dependent anion channel-1 modulates apoptotic cell death, 2005, Cell Death and Differentiation, vol. 12, pp. 751-760.*
Ambion TechNotes 9(5): "More siRNA Vectors for RNA Interference", Oct. 2002, accessed http://www.ambion.com/techlib/tn/95/952.html on Apr. 22, 2008, 4 print-out pages are enclosed.*
Elbashir et al., Aanlysis of gene function in somatic mammalian cells using small interfering RNAs, 2002, Methods, vol. 26, pp. 199-213.*
Gonzalez-Gronow et al., The voltage-dependent anion channel is a receptor for plasminogen kringle 5 on human endothelial cells, 2003, The Journal of Biological Chemistry, vol. 278, pp. 27312-27318.*
Liu et al., Increased susceptibility to apoptosis in CD45+ myeloma cells accompanied by the increased expression of VDAC1, 2006, Oncogene, vol. 25, pp. 419-429.*
Rostovtseva et al., ATP transport through a single mitochondrial channel, VDAC, studied by current fluctuation analysis, 1998, Biophysical Journal, vol. 74, pp. 2365-2373.*
Ricci et al., Mitochondrial functions during cell death, a complex (I-V) dilemma, 2003, Cell Death and Differentiation, vol. 10, pp. 488-492.*
Hamada et al., Effects on RNA interference in gene expression (RNAi) in cultured mammalian cells of mismathces and the introduction of chemical modifications at the 3' ends of siRNAs, 2002, Antisense and Nucleic Acid Drug Development, vol. 12, pp. 301-309.*

(Continued)

Primary Examiner — Dana Shin
(74) Attorney, Agent, or Firm — Rodney J. Fuller; Fennemore Craig, P.C.

(57) ABSTRACT

The present invention relates generally to the down regulation of mitochondrial protein, voltage-dependent anion channel (VDAC1), expression by RNAi or antisense therapy. In particular, the present invention is directed to VDAC1 silencing molecules useful in regulating cell proliferation and to pharmaceutical compositions comprising same useful in the treatment of diseases associated with aberrant cell proliferation.

4 Claims, 3 Drawing Sheets

OTHER PUBLICATIONS

Abu-Hammad et al., "The Expression Level of the Voltage-Dependent Anion Channel Controls Life and Death of the Cell", *PNAS*, 103(15):5787-5792 (Apr. 11, 2006).

Blachly-Dyson et al., "Cloning and Functional Expression in Yeast of Two Human Isoforms of the Outer Mitochondrial Membrane Channel, the Voltage-dependent Anion Channel", *The Journal of Biological Chemistry*, 268(3):1835-1841 (Jan. 25, 1993).

Lawen et al., "Voltage-Dependent Anion-Selective Channel 1 (VADC1)—a Mitochondrial Protein, rediscovered as a novel enzyme in the Plasma Membrane", *IJBCB*, 37:277-282 (2005).

International Search Report for PCT/IL2006/001176 dated Feb. 20, 2007 (4 pages).

International Preliminary Report on Patentability for PCT/IL2006/001176 dated Apr. 15, 2008 (8 pages).

Buettner R. et al., (2000) Evidence for secretory pathway localization of a voltage-dependent anion channel isoform. Proc Natl Acad Sci U S A. 28; 97(7):3201-3206.

Colombini M. (2004) VDAC: the channel at the interface between mitochondria and the cytosol. Mol Cell Biochem. 256/257: 107-115.

Czauderna F. et al., (2003) Structural variations and stabilising modifications of synthetic siRNAs in mammalian cells. Nucleic Acids Res. 31(11):2705-2716.

Godbole A. et al., (2003) VDAC1 is a conserved element of death pathways in plant and animal systems. Biochim. Biophys. Acta 1642:87-96.

Hammond S. M. (2005) Dicing and slicing: the core machinery of the RNA interference pathway. FEBS Lett. 579(26):5822-5829.

Ichim T. E. et al., (2004) RNA interference: a potent tool for gene-specific therapeutics. Am J Transplant 4:1227-1236.

Jiang M. et al., (2003) Bcl-2 constitutively suppresses p53-dependent apoptosis in colorectal cancer cells. Genes Dev 17:832-837.

Khachigian L. M. (2002) DNAzymes: cutting a path to a new class of therapeutics. Curr Opin Mol Ther 4(2), 119-121.

Liao X. et al., (2005) Small-interfering RNA-induced androgen receptor silencing leads to apoptotic cell death in prostate cancer. Mol Cancer Ther 4(4):505-515.

Milhavet O. et al., (2003) RNA interference in biology and medicine. Pharmacol Rev. 55(4):629-648.

Pillai O. et al., (2001) Polymers in drug delivery. Curr. Opin. Chem. Biol. 5:447-451.

Sapra P. et al., (2004) Improved outcome when B-cell lymphoma is treated with combinations of immunoliposomal anticancer drugs targeted to both the CD19 and CD20 epitopes. Clin Cancer Res. 10(7):2530-2537.

Shoshan-Barmatz V. et al., (2003). The voltage-dependent anion channel: characterization, modulation, and role in mitochondrial function in cell life and death. Cell Biochem Biophys 39:279-292.

Shoshan-Barmatz V. (2006). The Voltage-Dependent Anion Channel (VDAC): Function in Intracellular Signalling, Cell Life and Cell Death. Current Pharmaceutical design. 12(18):2249-2270.

Siolas D. et al., (2005) Synthetic shRNAs as potent RNAi triggers. Nat Biotechnol 23(2):227-31.

Tong A. W. et al., (2005) Small interfering RNA for experimental cancer therapy. Curr Opin Mol Ther 7:114-24.

Ui-Tei K. et al., (2004) Guidelines for the selection of highly effective siRNA sequences for mammalian and chick RNA interferenceNucl. Acids. Res. 32(3):936-948.

Welch P. J. et al., (1998) Expression of ribozymes in gene transfer systems to modulate target RNA levels. Curr Opin Biotechnol 9:486-496.

Zaid H. et al., (2005). The voltage-dependent anion channel-1 modulates apoptotic cell death. Cell Death Diff. 12(7):751-760.

\* cited by examiner

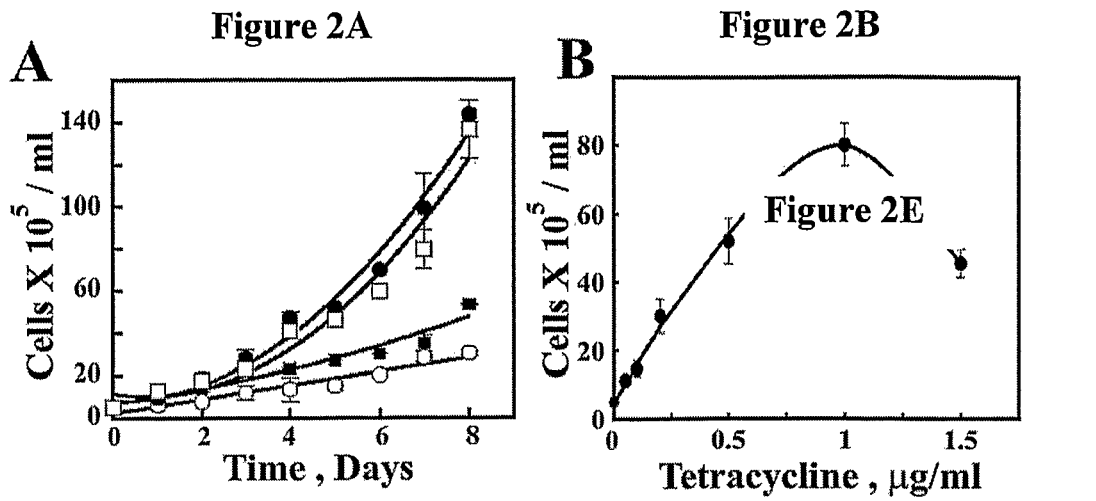
Figure 2A
Figure 2B
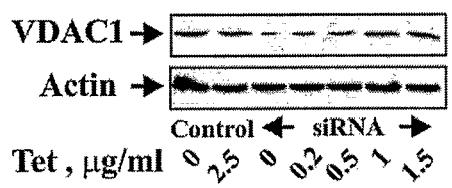
Figure 2C
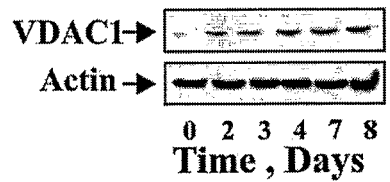
Figure 2D
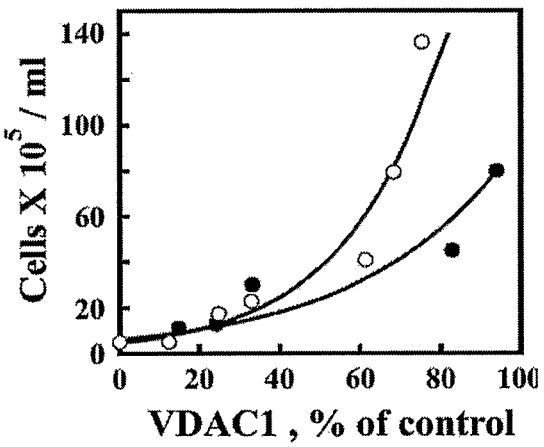
Figure 2E ATP synthesis ATP and ADP content Citrate synthase

COMPOSITIONS FOR SILENCING THE EXPRESSION OF VDAC1 AND USES THEREOF

RELATED APPLICATION DATA

This application is the U.S. national stage of PCT/IL2006/001176 filed on Oct. 15, 2006, which is based on and claims the benefit of U.S. Provisional Application No. 60/724,794 filed on Oct. 11, 2005 the content of each of which is expressly incorporated herein in its entirety by this reference.

FIELD OF THE INVENTION

The present invention relates in general to a method for silencing the expression of the mitochondrial protein voltage-dependent anion channel 1 (VDAC1). In particular, the present invention is directed to compounds including antisense and RNA interfering (RNAi) molecules targeted to a VDAC1 gene or a transcript thereof and therapeutic compositions comprising same, which are capable of silencing VDAC1 expression, useful in the treatment of diseases associated with aberrant cell proliferation.

BACKGROUND OF THE INVENTION

VDAC

Voltage-dependent anion channel 1 (VDAC1; mitochondrial porin) is a pore-forming protein found in the outer mitochondrial membrane (OMM) in all eukaryotic cells controlling the fluxes of ions and metabolites between the mitochondria and the cytosol. VDAC is recognized as a key protein in mitochondria-mediated apoptosis due to its function in the release of apoptotic proteins located in the intermembranal space and its interaction with apoptotic proteins (Shoshan-Barmatz et al, 2006). VDAC also serves as binding sites for several cytosolic enzymes and mitochondrial intermembranal space proteins, including hexokinase, creatine kinase and glycerol kinase.

Three mammalian isoforms of VDAC are known, VDAC1, VDAC2, VDAC3, where VDAC1 is the major isoform expressed in mammalian cells. Blachly-Dysion et al (1993) disclosed the cloning and functional expression in yeast of two human VDAC isoforms, VDAC1 and VDAC2. U.S. Pat. No. 5,780,235 discloses HACH (human voltage-dependent anion channel), subsequently identified as VDAC3. That patent provides genetically engineered expression vectors, host cells containing the vector, a method for producing HACH and a method for identifying pharmaceutical compositions inhibiting the expression and activity of HACH and for the use of such compositions for the treatment of cancer and proliferative diseases.

Mitochondria play an important role in the regulation of apoptotic cell death. The release of apoptogenic intermediates such as cytochrome c from the intermembranal space into the cytoplasm of a cell initiates a cascade of caspase activation that executes the cell death program. Substantial evidence links VDAC to apoptosis and suggests that VDAC is a critical player in the release of apoptogenic proteins from mitochondria in mammalian cells (Shoshan-Barmatz and Gincel, 2003; Shoshan-Barmatz et al, 2006).

It is well known that effective exchange of metabolites between mitochondria and the cytoplasm is essential for cell physiology. The key step of the exchange is transport across the outer mitochondrial membrane (OMM), which is mediated by VDAC (Colombini, 2004). The permeability of VDAC is regulated to adjust its activity to the actual cell's needs (Shoshan-Barmatz et al, 2006).

Certain compositions related to VDAC and use thereof for either inhibiting or inducing apoptosis are known in the art. International Patent Application No. PCT/IL2006/000311, to some of the inventors of the present application discloses VDAC1 specific apoptosis inducing peptides, which are useful in the treatment of diseases associated with aberrant apoptosis.

US Patent Application Publication No. 20050234116 discloses small molecule compounds with utility as VDAC regulators, in particular as apoptosis suppressors.

Gene Silencing

The down regulation of specific gene expression in a cell can be effected by oligonucleic acids using techniques known as antisense therapy and RNA interference (RNAi).

Antisense therapy refers to the process of inactivating target DNA or mRNA sequences through the use of complementary DNA or RNA oligonucleotides, thereby inhibiting gene transcription or translation. An antisense molecule can be single stranded, double stranded or triple helix.

RNA interference refers to the process of sequence-specific post-transcriptional gene silencing in eukaryotic cells mediated by RNA fragments. The process of post-transcriptional gene silencing is thought to be an evolutionarily conserved defense mechanism used by cells to prevent the expression of foreign genes and is commonly shared by diverse organisms.

RNAi can be induced in a cell by different species of double stranded RNA molecules, including short interfering RNA (siRNA) and short hairpin RNA (shRNA). In RNAi, one strand of double-stranded RNA molecule has the ribo-oligonucleotide sequence that is identical or substantially identical to the nucleotide sequence in the targeted mRNA transcript; the second strand of RNA has a complementary sequence to that in the target mRNA. Without wishing to be bound to theory, it is accepted that once the siRNAs are introduced into a cell or are generated from longer dsRNAs in the cell by the RNaseIII like enzyme, the siRNA associates with a protein complex, known as the RNA-induced silencing complex (RISC). The RISC then guides the small double stranded siRNA to the mRNA where the two strands of the double stranded siRNA separate, the antisense strand associates with the mRNA and a nuclease cleaves the mRNA at the site where the antisense strand of the siRNA binds (Hammond et al., 2005). The mRNA is subsequently further degraded by cellular nucleases. siRNAs appear to suppress gene expression without producing non-specific cytotoxic responses. Short hairpin RNAs have been shown to be potent RNAi triggers and in some instances maybe more effective than siRNA molecules (Siolas, et al., 2005). shRNAs may be produced by chemical synthesis as well as recombinant methods.

U.S. Pat. No. 6,506,559 teaches methods for inhibiting gene expression in vitro using siRNA constructs that mediate RNAi. International Patent Publication Nos. WO 02/055692, WO02/055693, and WO 00/44895 describe certain methods for inhibiting gene expression using RNAi. International Patent Publication Nos. WO 99/49029 and WO 01/70949 describe various vectors expressing siRNA molecules. International Patent Publication No. WO 2006/060454 teaches methods of designing small interfering RNAs, antisense polynucleotides, and other hybridizing nucleotides. US Patent Application Publication No. 20060217331 discloses chemically modified double stranded nucleic acid molecules for RNA interference.

There remains an unmet need for therapeutic agents effective in attenuating or inhibiting cellular proliferation in particular for the treatment of hyper-proliferative disease. The art neither teaches nor suggests inhibiting cell proliferation by silencing VDAC1.

SUMMARY OF THE INVENTION

The present invention provides compounds, which are capable of silencing expression of voltage-dependent anion channel 1 (VDAC1), compositions comprising same and methods of thereof in treating diseases and disorders associated with hyperproliferation. Suitable VDAC1 silencing compounds include antisense oligonucleotides, RNA interference (RNAi) molecules including dsRNA, siRNA, shRNA; and enzymatic nucleic acid molecules. The compounds are useful in the preparation of a pharmaceutical composition useful in treating diseases and disorders associated with aberrant cellular proliferation.

The invention is based in part on the unexpected discovery that down regulation of VDAC1 expression attenuates cellular proliferation (Abu-Hamad, et al., 2006). This effect is particularly surprising in view of the observation made by one of the inventors that overexpression of VDAC1 triggers apoptotic cell death (Zaid, et al, 2005).

Accordingly, the present invention provides a VDAC1 silencing molecule comprising at least one oligonucleotide sequence substantially complementary to one region of the gene or transcript encoding voltage dependent anion channel 1 (VDAC1), pharmaceutical compositions comprising same and methods of use thereof.

According to one aspect the present invention provides a molecule selected from the group consisting of a) a RNAi oligonucleotide; b) an antisense oligonucleotide; and c) an enzymatic oligonucleotide; wherein the oligonucleotide comprises at least one nucleic acid sequence sufficiently complementary to a target sequence of about 12 to about 100 nucleotides of a VDAC1 gene or transcript.

In various embodiments the RNAi oligonucleotide is selected from shRNA and siRNA, a derivative, analog or salt thereof useful for attenuation or inhibiting cellular proliferation, in diseases and disorders associated with aberrant cell proliferation.

According to one embodiment the present invention provides a RNA interference (RNAi) molecule that silences expression of VDAC1, wherein the RNAi molecule comprises:
  a. a first ribo-oligonucleotide sequence substantially identical to a target sequence of about 12 to about 100 nucleotides of a VDAC1 transcript; and
  b. a second ribo-oligonucleotide sequence substantially complementary to the first ribo-oligonucleotide;
  wherein said first and second ribo-oligonucleotide sequences are annealed to each other to form the RNAi molecule.

In some embodiments the RNAi molecule is a single-stranded short hairpin RNA (shRNA) wherein the first ribo-oligonucleotide sequence is separated from the second ribo-oligonucleotide sequence by a linker which forms a loop structure upon annealing of the first and second ribo-oligonucleotide sequences. In some embodiments the linker is about 3 to about 60 nucleotides.

In some embodiments the RNAi molecule is a double stranded small interfering RNA (siRNA) wherein the first and the second ribo-oligonucleotide sequences are located on separate strands, and wherein said strands are capable of annealing to each other to form said double stranded siRNA molecule.

According to some embodiments, the first and second ribo-oligonucleotide strands each comprise about 12 to about 100 ribonucleotides; preferably about 12 to about 50 ribonucleotides. In some embodiments each ribo-oligonucleotide strand comprises about 17 to about 28 ribonucleotides. In other embodiments each ribo-oligonucleotide strand comprises about 19 to about 21 ribo-oligonucleotides. A ribo-oligonucleotide strand comprising one or more non-natural ribo-oligonucleotides is encompassed in the scope of the invention.

According to further embodiments, the first ribo-oligonucleotide strand has at least 90% sequence identity to a target sequence of about 12 to about 100 nucleotides of a the VDAC1 mRNA transcript. In some embodiments the first ribo-oligonucleotide strand has at least 95% or preferably 100% sequence identity to a target sequence of about 12 to about 100 nucleotides of the VDAC1 mRNA transcript.

In some embodiments VDAC1 is human VDAC1 having a polypeptide sequence set forth in SEQ ID NO:1. An example of a polynucleotide encoding human VDAC1 is a VDAC1 mRNA transcript set forth herein as SEQ ID NO:4, and a VDAC coding sequence set forth in SEQ ID NO:5.

In some embodiments the first ribo-oligonucleotide comprises a sequence set forth in SEQ ID NO:6.

In various embodiments the RNAi molecule comprises a first ribo-oligonucleotide having a sequence set forth in SEQ ID NO:6 and a second ribo-oligonucleotide sequence is set forth in SEQ ID NO:7.

In certain embodiments the RNAi molecule is an shRNA molecule comprising an oligonucleotide sequence set forth in SEQ ID NO:10.

In some embodiments the antisense oligonucleotide is selected from antisense RNA, antisense DNA, derivatives, analogs or salt thereof.

According to one embodiment, the present invention provides an antisense oligonucleotide comprising about 12 to about 100 nucleotides in length, wherein the oligonucleotide is complementary to a target sequence of about 12 to about 100 nucleotides of a nucleic acid molecule encoding VDAC1. In certain embodiments the antisense oligonucleotide is from about 12 up to about 100 nucleotides, and may be in single stranded, double stranded or triple helix form.

In some embodiments the antisense molecule comprises an oligonucleotide sequence set forth in any one of SEQ ID NO:6-9.

In some embodiments VDAC1 is a mammalian VDAC1 sequence. In preferred embodiments VDAC1 is human VDAC1 having a polypeptide sequence set forth in SEQ ID NO:1. In some embodiments the polynucleotide encoding VDAC1 is set forth in any one of SEQ ID NOs:4 or 5.

In some embodiments the VDAC1 target sequence is selected from an oligonucleotide sequence comprising about 12 to about 100 contiguous nucleotides of VDAC1 gene or VDAC1 mRNA set forth in SEQ ID NO:4. In some embodiments the target sequence comprises a nucleotide sequence comprising about 12 to about 50 contiguous nucleotides, or about 17 to about 28 contiguous nucleotides of VDAC1 coding sequence, set forth in SEQ ID NO:4. In yet other embodiments the VDAC1 target sequence is set forth in any one of SEQ ID NO:6 or 7.

In another aspect the present invention provides a polynucleotide construct comprising a DNA oligonucleotide expressing a VDAC1 silencing molecule of the present invention. In some embodiments the polynucleotide construct comprises a DNA oligonucleotide expressing a VDAC1 silencing molecule, wherein the DNA oligonucleotide is operably linked to a promoter element. In some embodiments the polynucleotide construct comprises an oligonucleotide having a sequence set forth in any one of SEQ ID NOs: 8-9 and 11-13.

The polynucleotide construct expresses an oligonucleotide capable of down regulating or silencing VDAC1 expression.

In some embodiments the polynucleotide construct is a mammalian RNA expression vector comprising a DNA oligonucleotide expressing a VDAC1 silencing molecule of the present invention, wherein the DNA oligonucleotide is operably linked to a promoter element.

Further provided is a host cell comprising a polynucleotide construct of the present invention. In various embodiments the host cell is a bacterial or yeast cell. In other embodiments the host cell is a mammalian cell.

According to another aspect the present invention provides a pharmaceutical composition comprising a VDAC1 silencing compound; and a pharmaceutically acceptable carrier. In some embodiments the VDAC1 silencing compound is selected from a VDAC1 antisense molecule, a VDAC1 RNAi molecule, a VDAC1 antisense expression vector, a VDAC1 RNAi expression vector, cells expressing a VDAC1 antisense molecule, cells expressing a RNAi molecule.

The principles of the present invention are exemplified in both in vitro and in vivo model systems of diseases associated with aberrant proliferation. In some embodiments VDAC1 may be selected from the group consisting of a mammalian VDAC1 isoform, a yeast VDAC1 isoform and a plant VDAC. In various embodiments VDAC1 is a mammalian VDAC1, preferably human VDAC1.

In another aspect the present invention provides a method for silencing voltage-dependent anion channel 1 (VDAC1) expression in a cell comprising the step of administering to the cell an effective amount of a VDAC1 expression inhibitor selected from a) an antisense oligonucleotide; b) a RNAi oligonucleotide; and c) an enzymatic oligonucleotide; wherein the oligonucleotide comprises at least one sequence sufficiently complementary to a target sequence of about 12 to about 100 nucleotides of a nucleic acid molecule encoding VDAC1 thereby silencing VDAC1 expression.

In another aspect the present invention provides a method for the treatment of a condition associated with aberrant proliferation, comprising administering to a subject in need thereof a therapeutically effective amount of at least one VDAC1 expression inhibitor selected from a) an antisense oligonucleotide; b) a RNAi oligonucleotide; and c) an enzymatic oligonucleotide; wherein the oligonucleotide comprises a sequence sufficiently complementary to a target sequence of about 12 to about 100 nucleotides of a nucleic acid molecule encoding VDAC1 thereby silencing VDAC1 expression.

In some embodiments aberrant cell proliferation is associated with hyperproliferative disease selected from the group consisting of tumor formation, primary tumors, tumor progression and tumor metastasis. In some embodiments the condition associated with aberrant cell proliferation is cancer. The compositions and methods of the invention are applicable to the treatment of breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, leukemias, lymphomas, gliomas, or multi-drug resistant cancer.

In some embodiments the disease is selected from cancers previously exhibiting chemo- and radiotherapy-resistance.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1A: Immunoblot analyses of hVDAC1 and actin expression in control and various stable hVDAC1-shRNA-T-REx-293 colonies. FIG. 1B: Immunocytochemical analysis of VDAC1 expression in control, and VDAC1-shRNA expressing cells. FIG. 1C: Quantitative analysis of cell growth rates of control and VDAC1 and shRNA-expressing cells followed by Trypan-Blue staining.

FIGS. 2A-2E show that murine VDAC1 (mVDAC1) expression in stably expressing shRNA cells restores cell growth. FIG. 2A: Growth of control cells and hVDAC1-shRNA-expressing cell transfected with tetracycline inducible mVDAC1. FIG. 2B: Cell growth of hVDAC1-shRNA expressing cells transfected with mVDAC1 as a function of tetracycline concentration. The VDAC1 expression level on day six was analyzed in cell extracts using anti-VDAC1 or anti-actin antibodies as a function of the indicated tetracycline concentration (2C) or as a function of time (2D). FIG. 2E: Quantitative analysis of immunoblots representing mVDAC1 expression level as a function of tetracycline concentration or of growth time.

FIG. 3A: ATP synthesis was assayed. ATP (black) and ADP (grey) content, determined using luciferin/luciferase (3B) and the citrate synthase activity (3C) of cell extracts were assayed. ATP levels and cell growth were analyzed in hVDAC1-shRNA expressing cells further expressing mVDAC1 under the control of different concentrations of tetracycline (3D). The inset shows the same results presented as cell growth as a function of the cellular ATP level.

DETAILED DESCRIPTION OF THE INVENTION

Figure 1A:
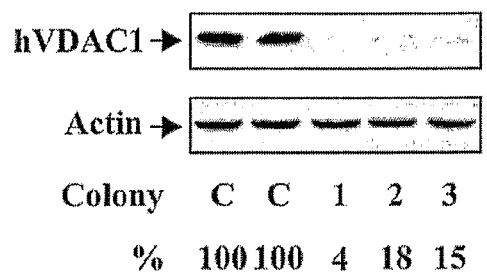
FIGS. 1A-1C show reduction of hVDAC1 expression and cell growth in VDAC1 shRNA expressing cells. T-REx-293 cells were transfected with 19 bp of the human VDAC1 sequence to suppress endogenous hVDAC1 expression.

The present invention relates to VDAC1 silencing molecules. In particular the present invention provides antisense, RNAi and enzymatic nucleic acid molecules directed to VDAC1, compositions comprising same and methods useful for attenuating or inhibiting cell proliferation in diseases and disorders associated with aberrant cell proliferation. Without wishing to be bound to theory, the inhibition of VDAC1 activity or down regulation of its expression reduces cell ATP supply, and in turn leads to cell death. The present invention is based in part on experimental systems that provide evidence of the function of VDAC1 in regulating cell life and death including the establishment of VDAC1-knocked-down cell lines expressing shRNA, in which the expression of endogenous VDAC1 was reduced by about 90% (Abu-Hamad, et al, 2006).

According to one aspect there is provided an antisense or RNAi molecule useful for silencing VDAC1 expression. In another aspect VDAC1 silencing molecules have utility in the treatment of proliferative disease, including cancer.

DEFINITIONS

For convenience certain terms employed in the specification, examples and claims are described herein.

Three VDAC isoforms, encoded by three genes, are known to date. The term "VDAC1" as used herein and in the claims refers to the VDAC1 isoform and the corresponding polynucleotides.

The protein sequences of the human, mouse and rat VDAC1 isoforms are provided in the sequence listing herein below.

Human VDAC1 set forth in SEQ ID NO:1, (NP_003365) is a 283 amino acid protein; located on chromosome 5 position q31. A VDAC1 mRNA transcript polynucleotide sequence is set forth in SEQ ID NO:4. Variations of that sequence are encompassed in the present application, due to naturally occurring polymorphisms in the human population and the degeneracy of the genetic code. The coding polynucleotide is set forth in SEQ ID NO:5. The entire gene (32,827 bases) including untranslated and coding regions has Genbank accession number NC_000005.

Rat VDAC1 set forth in SEQ ID NO:2 (NP_112643) is a 283 amino acid protein;

Mouse VDAC1 set forth in SEQ ID NO:3 (NP_035824) is a 283 amino acid protein. Two murine splice variants of VDAC1 have been identified. One has a leader peptide of 13 amino acids at the amino terminus and is primarily targeted through the golgi to the cell membrane. The variant is also known as plasmalemmal VDAC1, or PlVDAC1 (Buettner et al., 2000). The second splice variant lacks the leader peptide and is translocated to the outer mitochondrial membrane.

The terms "oligonucleotide" and "oligonucleic acid" are used interchangeably and refer to an oligomer or polymer of ribonucleic acid (ribo-oligonucleotide) or deoxyribonucleic acid comprising up to about 100 nucleic acid residues. These terms include nucleic acid strands composed of naturally-occurring nucleobases, sugars and covalent intersugar linkages as well as oligonucleotides having non-naturally-occurring portions which function similarly. Such modified or substituted oligonucleotides may be preferred over native forms because of the valuable characteristics including, for example, increased stability in the presence of plasma nucleases and enhanced cellular uptake.

The term "RNAi molecule" or "RNAi oligonucleotide" refers to single- or double-stranded RNA molecules having a total of about 15 to about 100 bases, preferably from about 30 to about 60 bases and comprises both a sense and antisense sequence. For example the RNA interference molecule can be a double-stranded polynucleotide molecule comprising self-complementary sense and antisense regions, wherein the antisense region comprises complementarity to a target nucleic acid molecule. Alternatively the RNAi molecule can be a single-stranded hairpin polynucleotide having self-complementary sense and antisense regions, wherein the antisense region comprises complementarity to a target nucleic acid molecule or it can be a circular single-stranded polynucleotide having two or more loop structures and a stem comprising self-complementary sense and antisense regions, wherein the antisense region comprises complementarity to a target nucleic acid molecule, and wherein the circular polynucleotide can be processed either in vivo or in vitro to generate an active molecule capable of mediating RNAi.

A "polynucleotide" as used herein refers to DNA or RNA of genomic or synthetic origin, having more than about 100 nucleic acids.

The terms "enzymatic nucleic acid molecule" or "enzymatic oligonucleotide" refers to a nucleic acid molecule which has complementarity in a substrate binding region to a specified gene target, and also has an enzymatic activity which is active to specifically cleave target VDAC1 RNA, thereby silencing VDAC1. The complementary regions allow sufficient hybridization of the enzymatic nucleic acid molecule to the target RNA and subsequent cleavage. The term enzymatic nucleic acid is used interchangeably with for example, ribozymes, catalytic RNA, enzymatic RNA, catalytic DNA, aptazyme or aptamer-binding ribozyme, catalytic oligonucleotide, nucleozyme, DNAzyme, RNAenzyme. The specific enzymatic nucleic acid molecules described in the instant application are not limiting and an enzymatic nucleic acid molecule of this invention requires a specific substrate binding site which is complementary to one or more of the target nucleic acid regions, and that it have nucleotide sequences within or surrounding that substrate binding site which impart a nucleic acid cleaving and/or ligation activity to the molecule. U.S. Pat. No. 4,987,071 discloses examples of such molecules.

"Complementarity" refers to the ability of a nucleic acid to form hydrogen bond(s) with another nucleic acid sequence. A percent complementarity indicates the percentage of contiguous residues in a nucleic acid molecule which can form hydrogen bonds (e.g., Watson-Crick base pairing) with a second nucleic acid sequence. "Fully complementary" means that all the contiguous residues of a nucleic acid sequence will hydrogen bond with the same number of contiguous residues in a second nucleic acid sequence. The term "substantially" complementary as used herein refers to a molecule in which about 80% of the contiguous residues of a nucleic acid sequence will hydrogen bond with the same number of contiguous residues in a second nucleic acid sequence. In some embodiments substantially complementary refers to 85%, 90%, 95% of the contiguous residues of a nucleic acid sequence hydrogen bonding with the same number of contiguous residues in a second nucleic acid sequence.

The ribo-oligonucleotide strands according to the present invention each comprise from about 12 to about 100 nucleotides, preferably from about 12 to about 50 nucleotides. In some embodiments the ribo-oligonucleotides of the present invention each comprise from about 17 to about 28 nucleotides. In other, embodiments each ribo-oligonucleotide strand comprises about 19 to about 21 oligonucleotides. The ribo-oligonucleotides according to the invention can be produced synthetically or by recombinant techniques.

The term "expression vector" and "recombinant expression vector" as used herein refers to a DNA molecule, for example a plasmid or virus, containing a desired and appropriate nucleic acid sequences necessary for the expression of the operably linked RNAi sequence for expression in a particular host cell. A suitable example includes a plasmid with a sequence encoding a small hairpin RNA (shRNA) under the control of an RNA Polymerase III (Pol III) promoter. A particularly suitable vector directs expression of a VDAC1 antisense or RNAi molecule when introduced into a cell, thereby reduce the levels of endogenous VDAC1 expression.

As used herein "operably linked" refers to a functional linkage of at least two sequences. Operably linked includes linkage between a promoter and a second sequence, for example an oligonucleotide of the present invention, wherein the promoter sequence initiates and mediates transcription of the DNA sequence corresponding to the second sequence.

Methods for manipulating the vector nucleic acid are well known in the art and include for example direct cloning. In this manner, an expression vector can be constructed such that it can be replicated in any desired cell, expressed in any desired cell, and can even become integrated into the genome of any desired cell.

The term "expression product" is used herein to denote a VDAC1 antisense or RNAi oligonucleotide. A VDAC1 RNAi expression product is preferably siRNA or shRNA.

A human VDAC1 mRNA transcript polynucleotide sequence is set forth in SEQ ID NO4. A DNA polynucleotide sequence of the human VDAC1 coding region is set forth in SEQ ID NO:5.

As used herein, the terms "target" or "target sequence" refer to the nucleic acid sequence that is selected for silencing expression. The target sequence can be RNA or DNA, and may also refer to a polynucleotide comprising the target sequence.

The present invention also provides pharmaceutical formulations, both for veterinary and for human medical use, which comprise as the active agent one or more of the VDAC1 nucleic acid molecules described in the invention, for the manufacture of a medicament for the treatment or prophylaxis of the conditions variously described herein.

The terms "inhibit" or "down-regulate" or "silence" VDAC1 expression refer to a reduction in the expression of the gene, or level of RNA or equivalent RNA encoding the protein or the level of the protein, below the level that is observed in the absence of the nucleic acid molecules of the invention. In some embodiments gene expression is down-regulated by at least 50%, at least 70%, 80% and preferably by at least 90%.

Antisense Molecules

Antisense technology is the process in which an antisense RNA or DNA molecule interacts with a target sense DNA or RNA strand. A sense strand is a 5' to 3' mRNA molecule or DNA molecule. The complementary strand, or mirror strand, to the sense is called an antisense. When an antisense strand interacts with a sense mRNA strand, the double helix is recognized as foreign to the cell and will be degraded, resulting in reduced or absent protein production. Although DNA is already a double stranded molecule, antisense technology can be applied to it, building a triplex formation.

RNA antisense strands can be either catalytic or non-catalytic. The catalytic antisense strands, also called ribozymes, cleave the RNA molecule at specific sequences. A non-catalytic RNA antisense strand blocks further RNA processing.

Antisense modulation of VDAC1 levels in cells and tissues may be effected by contacting the cells and tissues with at least one antisense compound, including antisense DNA, antisense RNA, a ribozyme, DNAzyme, a locked nucleic acid (LNA) and an aptamer. In some embodiments the molecules are chemically modified. Antisense (AS) technology and its enormous therapeutic potential has been reviewed extensively (Milhavet, 2003). In certain specific embodiments the antisense molecule is an antisense RNA oligonucleotide or an oligonucleotide analog thereof comprising from about 8 to about 50 nucleotides. In some embodiments the antisense RNA is about 10 to about 25 nucleotides long.

In other embodiments the antisense molecule is antisense DNA or an antisense DNA analog. Methods of producing antisense oligonucleotides may be found for example, in U.S. Pat. Nos. 7,022,832; 6,972,171; 6,277,981 and US Patent Application Publication No. 20050261485.

RNAi Oligonucleotide Molecules

Guidelines for the selection of highly effective siRNA sequences for mammalian and chick RNA may be found, inter alia, in Kumiko (2004) and in US Patent Application Publication No. 20060078902

A RNAi oligonucleotide molecule of the invention can be unmodified or chemically-modified. A RNAi oligonucleotide molecule of the instant invention can be chemically synthesized, expressed from a vector or enzymatically synthesized. The instant invention also features various chemically-modified RNAi oligonucleotide molecules capable of silencing VDAC1 gene expression in cells by RNA inference (RNAi). The use of chemically-modified RNAi oligonucleotide molecule is expected to improve various properties of native RNAi oligonucleotide molecules through increased resistance to nuclease degradation in vivo and/or improved cellular uptake. The RNAi oligonucleotide molecules of the present invention provide useful reagents and methods in therapeutic, diagnostic, agricultural, target validation, genomic discovery, genetic engineering and pharmacogenomic applications.

In one embodiment, the invention features one or more RNAi oligonucleotide molecules and methods that independently or in combination modulate the expression of gene(s) encoding voltage dependent anion channel. In one embodiment, the present invention features RNAi oligonucleotide molecules that modulate the expression of human VDAC1 (for example SEQ ID NO:1). VDAC1 has been cloned from human, rat, mouse, yeast and plant sources, therefore coding sequence information for VDAC1 is available from gene and protein databases, including the GenBank database.

In one embodiment, the invention features a RNAi oligonucleotide molecule that down regulates expression voltage-dependent anion channel 1 (VDAC1) gene by RNA interference. A RNAi oligonucleotide molecule of the invention can comprise any contiguous VDAC1 sequence (e.g., about 12 to about 50 contiguous VDAC1 nucleotides). The target VDAC1 sequence can be selected from coding or non-coding regions of the gene. In one embodiment, the invention features a RNAi oligonucleotide molecule comprising ribo-oligonucleotide sequences set forth in SEQ ID NO:6. and 7. In some embodiments the present invention provides an antisense oligonucleotide comprising at least one of the oligonucleotide set forth in SEQ ID NOs:6-9.

The antisense and RNAi molecules can be prepared using synthetic or recombinant techniques known in the art. For example, the oligonucleotides of the present invention can be synthesized separately and joined together post-synthetically, for example, by ligation following synthesis and/or deprotection. The RNAi molecules of the invention can also be synthesized via a tandem synthesis methodology wherein both RNAi strands are synthesized as a single contiguous oligonucleotide fragment or strand separated by a cleavable linker which is subsequently cleaved to provide separate RNAi fragments or strands that hybridize and permit purification of the RNAi duplex. The linker can be a polynucleotide linker or a non-nucleotide linker.

The synthesis of oligonucleotides as described herein can be readily adapted to large scale synthesis platforms employing batch reactors, synthesis columns and the like.

A RNAi oligonucleotide can also be assembled from two distinct nucleic acid strands or fragments wherein one fragment includes the sense region and the second fragment includes the antisense region of the RNA molecule. RNAi molecules and methods for producing RNAi oligonucleotides can be found for example in US Patent Application Publication Nos. 20050100907, 20020137210 and the like.

Synthesis of RNAi molecules suitable for use with the present invention can be effected as follows. First, the VDAC1 mRNA sequence is scanned downstream of the AUG start codon for AA-dinucleotide sequences. Occurrence of each AA and the 19 3'-adjacent nucleotides is recorded as a potential RNAi target site. Preferably, RNAi target sites are selected from the open reading frame (ORF), however, that RNAi molecules directed at un-translated regions (UTR) may also be effective.

Second, potential target sites are compared to an appropriate genomic database (e.g., human, mouse, rat, etc.) using any sequence alignment software, such as the BlastN software available from the NCBI server. Putative target sites that exhibit significant homology to other coding sequences are filtered out.

Qualifying target sequences are selected as templates for RNAi synthesis. Preferred sequences are those including low G/C content, as these have proven to be more effective in mediating gene silencing as compared with sequences including G/C content higher than 55%. Several target sites are preferably selected along the length of the target gene for evaluation. For better evaluation of the selected RNAi molecules, a negative control is preferably used in conjunction. Negative-control RNAi molecules preferably include the same nucleotide composition as the RNAi molecules s but lack significant homology to the genome. Thus, a scrambled nucleotide sequence of the RNAi is preferably used, provided it does not display any significant homology to any other gene.

Another agent capable of down regulating VDAC1 is a ribozyme molecule capable of specifically cleaving an mRNA transcript encoding VDAC1. Ribozymes have been used for the sequence-specific inhibition of gene expression by the cleavage of mRNAs encoding proteins of interest (Welch, et al. 1998).

The possibility of designing ribozymes to cleave any specific target RNA has rendered them valuable tools in both basic research and therapeutic applications. In therapeutics, ribozymes have been exploited to target viral RNAs in infectious diseases, dominant oncogenes in cancers, and specific somatic mutations in genetic disorders Ribozymes and ribozyme analogs are described, for example, in U.S. Pat. Nos. 5,436,330; 5,545,729 and 5,631,115.

Another agent capable of silencing a VDAC1 is a DNAzyme molecule, which is capable of specifically cleaving an mRNA transcript or a DNA sequence of VDAC1. DNAzymes are single-stranded polynucleotides that are capable of cleaving both single- and double-stranded target sequences (reviewed in Khachigian, 2002). Examples of construction and amplification of synthetic, engineered DNAzymes recognizing single- and double-stranded target cleavage sites are disclosed in U.S. Pat. No. 6,326,174.

Delivery of the VDAC1 Silencing Molecules

The antisense and RNAi molecules can be inserted into a host cell using one of a variety of techniques. Endocytosis relies on the cell's natural process of receptor mediated Endocytosis, which is typically slow and inefficient. Microinjection of the molecule is effective but time consuming.

The molecules of the present invention can be delivered to a cell by liposome encapsulation, which is effective but may be expensive. Liposome encapsulation can be achieved by using commercially available products to create a cationic phospholipid bilayer that will surround the nucleotide sequence. The resulting liposome then can merge with the cell membrane allowing the antisense or RNAi molecule to enter the cell.

In electroporation the antisense/RNAi molecule traverses the cell membrane after electric current is applied to the cells. Electroporation has been used for localized delivery to skin and muscle as it is effective with a variety of cell and species type and may be performed with intact tissue.

Delivery reagents that facilitate efficient antisense and RNAi entry into cells of a subject in need thereof include antisense/RNAi conjugates and complexes. Suitable molecules that serve as a conjugate include lipophilic units, inert polymers and peptides, that can be covalently linked to the antisense/RNAi molecule, aiding uptake into tissues. Several delivery reagents that complex siRNA to facilitate cellular uptake are cationic liposomes, dendrimers, polyethylene glycol (PEG) and atelocollagen. U.S. Pat. No. 6,841,539, incorporated discloses dermal and epidermal compositions useful for the topical delivery of nucleic acids, including antisense and RNAi molecules.

Liposomes have been relatively successful in cell culture, and have been shown to be useful in delivery of nucleic acids including siRNA. For example, US Patent Application Publication 20030099697 relates to amphoteric liposomes, which comprise positive and negative membrane-based or membrane-forming charge carriers as well as the use of liposomes. US Patent Application Publication No 20040142025 discloses a method for the preparation of liposomes encapsulating a therapeutic product.

Polymer-based dendrimers display greater transfection efficiency and low toxicity in many cell types, thus may have a greater potential for in vivo or in situ application. Finally, atelocollagen, a naturally occurring protein that is low in immunogenicity, is used clinically for a wide range of purposes. Atelocollagen has been shown to allow increased cellular uptake, nuclease resistance and prolonged release of genes and oligonucleotides. Chemical conjugates of atelocollagen display low-toxicity and low-immunogenicity when delivered.

In one embodiment of the invention a RNAi oligonucleotide molecule is adapted for use to treat disorders and diseases associated with aberrant cell proliferation, in particular cancer. A RNAi oligonucleotide molecule can comprise a sense region and an antisense region, wherein said antisense region can comprise sequence complementary to a RNA sequence encoding VDAC1 and the sense region can comprise sequence complementary to the antisense region. A RNAi oligonucleotide molecule can be assembled from two nucleic acid fragments wherein one fragment can comprise the sense region and the second fragment can comprise the antisense region of said RNAi oligonucleotide molecule. The sense and antisense regions can be covalently connected via a linker molecule. The linker molecule can be a polynucleotide or non-nucleotide linker. The sense region of a RNAi oligonucleotide molecule of the invention can comprise a 3'-terminal overhang and the antisense region can comprise a 3'-terminal overhang. The 3'-terminal overhangs each can comprise about 2 nucleotides. The antisense region 3'-terminal nucleotide overhang can be complementary to RNA encoding VDAC1. The sense region can comprise a terminal cap moiety at the 5'-end, 3'-end, or both 5' and 3' ends of the sense region.

In one embodiment, nucleic acid molecules of the invention are double-stranded RNA molecules. In another embodiment, the RNAi oligonucleotide molecules of the invention consist of duplexes or hairpin structures comprising about 12 to about 60 nucleotides either in both strands (siRNA) or in a single strand (shRNA) In yet another embodiment, RNAi oligonucleotide molecules of the invention comprise duplexes with overhanging ends of about 1 to about 3 nucleotides, for example about 21 nucleotide duplexes with about 19 base pairs and about 2 nucleotide 3'-overhangs.

In one embodiment, the invention features one or more chemically-modified RNAi oligonucleotide molecule constructs having specificity for VDAC1 expressing nucleic acid molecules. Chemical modifications may be useful in protecting a synthetic molecule from in vivo enzymatic degradation. Non-limiting examples of such chemical modifications include without limitation phosphorothioate internucleotide linkages, 2'-O-methyl ribo-oligonucleotides, 2'-O-methyl modified pyrimidine nucleotides, 2'-deoxy-2'-fluoro ribo-oligonucleotides, 2'-deoxy-2-fluoro modified pyrimidine nucleotides, "universal base" nucleotides, 5-C-methyl nucleotides, and inverted deoxy abasic residue incorporation. These chemical modifications, when used in various RNAi oligonucleotide molecule constructs, may preserve RNAi activity in cells and increase the serum stability of these compounds. For example, Czauderna et al. (2003) demonstrated that 2'-O-methyl modifications at specific positions in the molecule improve stability of siRNAs in serum and are tolerated without significant loss of RNA interference activity.

A "modified base" or modified nucleic acid refers to a nucleotide base other than adenine, guanine, cytosine, thymine and uracil at 1' position or their equivalents; such bases can be used at any position, for example, within the catalytic core of an enzymatic nucleic acid molecule and/or in the substrate-binding regions of the nucleic acid molecule.

In one embodiment, the invention features modified nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl substitutions.

The modifications may be incorporated during the synthesis of the RNAi oligonucleotide molecules. The antisense region of a RNAi oligonucleotide molecule of the invention can comprise a phosphorothioate internucleotide linkage at the 3' end of said antisense region. The antisense region can comprise between about one and about five phosphorothioate internucleotide linkages at the 5' end of said antisense region. The 3'-terminal nucleotide overhangs of a RNAi oligonucleotide molecule of the invention can comprise ribo-oligonucleotides or deoxyribo-oligonucleotides that are chemically-modified at a nucleic acid sugar, base, or backbone. The 3'-terminal nucleotide overhangs can comprise one or more universal base ribo-oligonucleotides and or one or more acyclic nucleotides. The RNAi molecule can be modified by lipid derivatization, as exemplified in US Patent Application Publication No. 20060178324, which teaches lipophilic derivatives of double stranded RNA molecules.

In yet another example, the introduction of one or more chemically-modified nucleotides into the nucleic acid molecules will assist in overcoming potential limitations of in vivo stability and bioavailability inherent to exogenously delivered RNA molecules. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. It is also thought that the administration of chemically-modified RNAi oligonucleotide molecule may minimize the possibility of activating interferon activity in humans.

In another aspect, the present invention provides an expression vector comprising a nucleic acid sequence encoding at least one RNAi oligonucleotide molecule of the invention thereby providing expression of the nucleic acid molecule. In another aspect, the present invention provides a cell expressing such a vector. The cell can be a mammalian cell, a prokaryotic cell or a plant cell. Preferably the cell is a human cell. The RNAi oligonucleotide molecule of the expression vector can comprise a sense region and an antisense region and the antisense region can comprise sequence complementary to a RNA sequence encoding EGFR and the sense region can comprise sequence complementary to the antisense region. The RNAi oligonucleotide molecule can comprise two distinct strands having complementarity sense and antisense regions. The RNAi oligonucleotide molecule can comprise a single-strand having complementary sense and antisense regions, for example shRNA. In one embodiment, the RNAi oligonucleotide molecule is a VDAC1 specific shRNA molecule.

In one embodiment, the present invention provides a method for down regulating the expression of a VDAC1 gene within a cell, comprising: (a) providing a RNAi oligonucleotide molecule of the invention, said molecule comprising a sequence complementary to a sequence of the VDAC1 mRNA; and (b) introducing the RNAi oligonucleotide molecule into a cell under conditions suitable to down regulate the expression of the VDAC1 gene in the cell. In some embodiments the RNAi molecule is chemically modified.

In one embodiment, the present invention provides a method for down regulating the expression of VDAC1 in a tissue explant, comprising: (a) providing a RNAi oligonucleotide molecule said molecule comprising a sequence complementary to a sequence of the VDAC1 mRNA; (b) introducing the RNAi oligonucleotide molecule into a cell of the tissue explant derived from a particular organism under conditions suitable to down regulate the expression of VDAC1 gene in the tissue explant. In some embodiments the tissue explant of step (b) is introduced back into the donor organism or into another organism under conditions suitable to down regulate the expression of the VDAC1 gene in that organism.

The term "target site" refers to a sequence within a target RNA to which cleavage mediated by a RNAi oligonucleotide molecule construct is directed.

According to another aspect the present invention provides a therapeutic composition comprising a RNAi oligonucleotide molecule of the invention; and a pharmaceutically acceptable carrier or diluent.

In another aspect the present invention relates to a method for treating or preventing a disease or condition associated with aberrant cell proliferation in a subject, comprising administering to the subject a composition of the invention under conditions suitable for the treatment or prevention of the disease or condition in the subject. In some embodiments the method is used alone or in combination with adjunct therapies or therapeutics compounds.

In another aspect the present invention provides a kit comprising a RNAi oligonucleotide molecule of the invention; and instructions for use thereof.

In one embodiment, the synthesis of a RNAi molecule of the invention comprises: (a) synthesis of two complementary strands of the RNAi molecule; (b) annealing the two complementary strands together under conditions suitable to obtain a double-stranded RNA molecule.

In another embodiment, synthesis of the two complementary strands of the RNAi molecule is by solid phase oligonucleotide synthesis. In yet another embodiment, synthesis of the two complementary strands of the RNAi molecule is by solid phase tandem oligonucleotide synthesis.

A nucleic acid molecule homolog can be produced using a number of methods known to those skilled in the art (see, for example, Sambrook et al., 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologs can be selected from a mixture of modified nucleic acids by screening for the function of the protein encoded by the nucleic acid with respect to the induction of an anti-viral response, for example by the methods described herein.

A polynucleotide or oligonucleotide sequence can be deduced from the genetic code of a protein, however, the degeneracy of the code must be taken into account, and nucleic acid sequences of the invention also include sequences, which are degenerate as a result of the genetic code, which sequences may be readily determined by those of ordinary skill in the art.

The phrase "operably linked" refers to linking a nucleic acid sequence to a transcription control sequence in a manner such that the molecule is able to be expressed when transfected (i.e., transformed, transduced or transfected) into a host cell. Transcription control sequences are sequences, which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in animal, bacteria, helminth, yeast and insect cells.

A nucleic acid molecule of the invention may be inserted into appropriate expression vector, i.e., a vector which contains the necessary elements for the transcription of the inserted sequence.

Vectors can be introduced into cells or tissues by any one of a variety of known methods within the art, including in vitro recombinant DNA techniques, synthetic techniques, and in vivo genetic recombination. Such methods are generally described in Sambrook et al., 1992; Ausubel et al., 2002.

Constitutive promoters suitable for use with the present invention are promoter sequences that are active under most environmental conditions and most types of cells, Mammalian expression vectors are commercially available. The ability to select suitable vectors according to the cell type transformed is well within the capabilities of the ordinarily skilled artisan and as such, no general description of selection considerations is provided herein.

Pharmaceutical Compositions

The present invention provides pharmaceutical compositions comprising a VDAC1 silencing compound; and a physiologically acceptable carrier.

Depending on the location of the tissue of interest, VDAC1 silencing molecules can be supplied in any manner suitable for the provision of RNA and or DNA molecules. Thus, for example, a composition containing a source of VDAC1 antisense or RNAi (i.e., a VDAC1 synthetic antisense or RNAi molecule, or VDAC1 antisense or RNAi expression vector, or cells expressing a VDAC1 antisense or RNAi sequence) can be introduced into tissue of interest (e.g., injected, or pumped as a continuous infusion, or as a bolus within a tumor or intercutaneous or subcutaneous site, applied to all or a portion of the surface of the skin, dropped onto the surface of the eye, etc.).

A "subject" refers to an animal, preferably a mammal, more preferably a human.

As used herein, a "pharmaceutical composition" refers to a preparation of one or more of the active ingredients described herein, i.e. an antisense molecule, an RNAi molecule an enzymatic nucleic acid, with other components such as physiologically suitable carriers and excipients. The purpose of a pharmaceutical composition is to facilitate administration of a compound to a subject.

Hereinafter, the phrases "therapeutically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Apart from other considerations, the fact that the novel active ingredients of the invention are nucleic acids, dictates that the formulation be suitable for delivery of these types of compounds. In general, DNA and RNA molecules may be less suitable for oral administration due to susceptibility to digestion by gastric acids or intestinal enzymes, but methods for oral administration of nucleic acid molecules are known in the art. For example, DNA and RNA molecules can be modified in order to provide or enhance oral bioavailability. The pharmaceutical composition of this invention may be administered by any suitable means, such as orally, topically, or parenterally including intranasal, subcutaneous, intramuscular, intravenous, intra-arterial, intraarticular, or intralesional administration. Ordinarily, intravenous (i.v.) administration will be preferred.

The molecules of the present invention as active ingredients are dissolved, dispersed or admixed in a diluent or excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those in the art (see, for example, Ansel et al., 1990; Gennaro, 1990). In addition, if desired, the composition can contain minor amounts of auxiliary substances such as wetting or emulsifying agents, pH buffering agents.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example, polyethylene glycol are generally known in the art.

An example of nasal and pulmonary delivery of a siRNA molecule is disclosed in US Patent Application Publication No. 20030157030.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs. For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the nucleic acid molecule and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of a compound effective to prevent, delay, alleviate or ameliorate symptoms of a disease of the subject being treated. Determination of a therapeutically effective amount is well within the capability of those skilled in the art.

Toxicity and therapeutic efficacy of the nucleic acid compounds described herein can be determined by standard pharmaceutical procedures in cell cultures or experimental animals, e.g., by determining the IC50 (the concentration which provides 50% inhibition) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

In one particularly preferred embodiment according to the present invention, the nucleic acid compounds are administered orally (e.g. as a syrup, capsule, or tablet). In certain embodiments, delivery can be enhanced by the use of protective excipients. Oligonucleotide molecules may be synthesized using modified linkages and sugars in order to enhance stability, half-life and bioavailability. Alternatively, this can be accomplished either by complexing the compound with a composition to render it resistant to acidic and enzymatic hydrolysis or by packaging the nucleic acid compound in an appropriately resistant carrier such as a liposome. Elevated serum half-life can be maintained by the use of sustained-release "packaging" systems. Such sustained release systems are well known to those of skill in the art. The foregoing formulations and administration methods are intended to be illustrative and not limiting. It will be appreciated that, using the teaching provided herein, other suitable formulations and modes of administration can be readily devised.

In addition to the aforementioned ingredients, the formulations of this invention may further include one or more accessory ingredient(s) selected from diluents, buffers, flavoring agents, binders, surface active agents, thickeners, lubricants, preservatives, including antioxidants, and the like.

According to some embodiments of the invention, the therapeutically effective amount of the VDAC1 nucleic acid compound is a dosage in a range from about 0.02 mg/kg to about 100 mg/kg. Preferably, the dosage of the VDAC1 amino acid sequence according to the present invention is in a range from about 0.05 mg/kg to about 10 mg/kg. It will be understood that the dosage may be an escalating dosage so that low dosage may be administered first, and subsequently higher dosages may be administered until an appropriate response is achieved. Also, the dosage of the composition can be administered to the subject in multiple administrations in the course of the treatment period in which a portion of the dosage is administered at each administration.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

In some embodiments the VDAC1 nucleic acid compound are delivered to cells as modified nucleic acid molecules, as detailed infra.

In other embodiments the inhibitory compounds of the present invention are delivered to cells in a non-viral gene delivery system. Particulate gene transfer systems are usually based on oligo- or polycationic carrier molecules which can condense nucleic acids by electrostatic interactions with their negatively charged phosphate backbone. The positive charge of cationic lipids leads to electrostatic interaction with the DNA, the lipidic moiety enables the hydrophobic collapse and the formation of so called 'lipoplexes'. Polycationic carrier molecules, like polylysine or polyethyleneimine (PEI) bind and condense DNA due to their high density of positive charges and result in the formation of so called 'polyplexes'. The surface of the delivery particle can be coated with hydrophilic polymers, e.g. polyethylene glycol (PEG), which prevent binding to plasma proteins, blood cells and the RES and also enables a prolonged circulation time in the blood stream.

In yet another embodiment, the inhibitory compounds of the present invention are delivered to cells in vesicles. Immunoliposomes have been described to allow targeted delivery of anticancer drugs into solid tumors (for review see Sapra and Allen et al, 2004). A current approach is the use of phospholipid vesicles (liposomes) to deliver oligonucleotides to cells (Akhtar et al., 1991). In addition to protecting oligonucleotides from enzymatic degradation, liposomes offer the potential to control and sustain their release.

The nucleic acid sequences and analogs thereof of the present invention can be administered to a subject following microencapsulation. Methods of preparing microcapsules are known in the art and include preparation from an assortment of materials including natural and synthetic materials.

Therapeutic Use

The present invention provides methods of treating disease associated with aberrant cell proliferation and use of the VDAC1 antisense and RNAi molecules to prepare a medicament useful in the treatment of those diseases. Accordingly, in one embodiment the invention relates to a method of treating tumors in a subject, the method comprising at least the steps of administering an effective amount of an agent that reduces VDAC1 expression.

As used herein the terms "treating" or "treatment" should be interpreted in their broadest possible context. Accordingly, "treatment" broadly includes amelioration of the symptoms or severity of a particular disorder, for example a reduction in the rate of cell proliferation, reduction in the growth rate of a tumor, partial or full regression of a tumor, or preventing or otherwise reducing the risk of metastases or of developing further tumors.

As used herein, a "therapeutically effective amount", or an "effective amount" is an amount necessary to at least partly attain a desired response. A person of ordinary skill in the art will be able without undue experimentation to determine an effective amount of a compound of this invention for a given disease or tumor.

As used herein, the phrase "diseases associated with aberrant cell proliferation" includes diseases and disorders in which timely growth arrest does not ensue and cells grow or proliferate without restraint, for example in proliferative diseases including malignant and benign neoplasias including cancer and tumor growth. In one embodiment of this method, the abnormal cell growth is cancer, including, but not limited to cancer of any one or more of the following organs and tissues: lung, bone, pancreatic, skin, head or neck, eye, uterus, ovary, rectum, anal region, stomach, colon, breast, fallopian tubes, endometrium, cervix, vagina, vulva, lymph including Hodgkin's and non-Hodgkin's and lymphocytic lymphomas, esophagus, small intestine, endocrine system, thyroid gland, parathyroid gland, adrenal gland, soft tissue, urethra, penis, prostate, blood including chronic or acute leukemia, bladder, kidney, central nervous system (CNS) including spinal axis tumors, brain stem glioma; pituitary.

In another embodiment of said method, said abnormal cell growth or aberrant proliferative is a benign proliferative disease, including, but not limited to, psoriasis, benign prostatic hypertrophy, proliferative retinopathy or restenosis and cellular expansions due to DNA viruses such as Epstein-Barr virus, African swine fever virus and adenovirus.

In one preferred embodiment the VDAC1 inhibitory molecules of the present invention are useful in preventing or alleviating a cell-proliferative disorder or a symptom of a cell-proliferative disorder. Cell-proliferative disorders and/or a symptom of a cell-proliferative disorder are prevented or alleviated by administering at least one VDAC1 antisense or RNAi oligonucleotide molecule to a subject.

In one preferred embodiment of the invention, the RNAi molecules of the present invention are useful for the preparation of a medicament for inhibiting proliferative diseases or disorders including tumor growth and tumor progression. In another embodiment of the invention, the compounds are useful for preventing, treating or inhibiting a cell proliferative disease or disorder. The cell proliferative disease can be malignant or benign. The compositions are useful for the treatment or prevention of non-solid cancers, e.g. hematopoietic malignancies such as, but not being limited to, all types of leukemia, e.g. chronic myelogenous leukemia (CML), acute myelogenous leukemia (AML), mast cell leukemia, chronic lymphocytic leukemia and acute lymphocytic leukemia, lymphomas, and multiple myeloma, as well as of solid tumors such as, but not being limited to, mammary, ovarian, prostate, colon, cervical, gastric, esophageal, papillary thyroid, pancreatic, bladder, colorectal, melanoma, small-cell lung and non-small-cell lung cancers, granulosa cell carcinoma, transitional cell carcinoma, vascular tumors, all types of sarcomas, e.g. osteosarcoma, chondrosarcoma, Kaposi's sarcoma, myosarcoma, hemangiosarcoma, and glioblastomas.

It is to be understood that the terms "treating a proliferative disease or disorder" as used herein in the description and in the claims, are intended to encompass tumor formation, primary tumors, tumor progression or tumor metastasis.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Materials and Methods

Abbreviations:
VDAC, Voltage-Dependent Anion Channel; mVDAC1, murine VDAC1; hVDAC1, human VDAC1; shRNA, short hairpin RNA.

Most reagents were purchased from Sigma (St. Louis, Mo., USA). Monoclonal anti-VDAC1 antibodies (clone 173/045) came from Calbiochem-Novobiochem (Nottingham, UK). Monoclonal antibodies against actin were from Santa Cruz Biotechnology (Santa Cruz, Calif., U.S.A). Horseradish peroxidase conjugated anti-mouse antibodies were obtained from Promega (Madison, Wis., U.S.A). Alexa-488-conjugated goat anti-mouse antibodies were from Molecular Probes (Leiden, Netherlands).

Construction of Plasmids

Numerous vectors and kits useful for the cloning and expression of RNAi, and algorithms for selecting a target sequence molecules are commercially available. Certain non-limiting examples of siRNA vectors include the GeneSuppressor™ System (Imgenex, Corp.); Lentiviral shRNAmir triggers (Open Biosystems) and the like. In one embodiment a polynucleotide construct of the present invention is provided as a pSUPERretro® plasmid encoding shRNA targeting hVDAC1. Specific silencing of the endogenous hVDAC1 was achieved using a shRNA-expressing vector. Nucleotides 159-177 of the hVDAC1 coding sequence were chosen as target for shRNA. This sequence is presented in Table 1, as are the analogous sequences of mVDAC1, hVDAC2 and hVDAC3. The hVDAC1-shRNA-encoding sequence was created using the two complimentary oligonucleotides indicated below, each comprising the 19 deoxyribonucleotide sequence corresponding to the target sequence of hVDAC1 mRNA (159-177) (AGUGACGGGCAGUCUGGAA; SEQ ID NO:6) followed by a short spacer and an antisense sequence of the target (SEQ ID NO:7):

```
Oligo 1:
                                          (SEQ ID NO:12)
GATCCCCAGTGACGGGCAGTCTGGAATTCAAGAGATTCCAGACTGCCCGT

CACTTTTTTA

Oligo 2:
                                          (SEQ ID NO:13)
GGGTCACTGCCCGTCAGACCTTAAGTTCTCTAAGGTCTGACGGGCAGTGA

AAAAATTCGA
```

The hVDAC1-shRNA-encoding sequence was cloned into the BglII and HindIII sites of the pSUPERretro® plasmid (OligoEngine, Seattle, Wash.), containing a puromycin resistance gene. Transcription of this sequence by RNA-polymerase III produces a hairpin (hVDAC1-shRNA) set forth in SEQ ID NO:10.

Construction of a plasmid for tetracycline-regulated expression of mVDAC1: The mVDAC1 coding sequence was cloned into the BamHI and EcoRV restriction sites of the pcDNA4/TO vector (Invitrogen) containing the zeocin resistance gene and two tetracycline operator sites within the human cytomegalovirus (CMV) immediate-early promoter to allow for tetracycline-regulated expression of the mVDAC1 in transfected cells.

Cell Culture

T-REx-293 cells: A transformed primary human embryonal kidney cell line (Invitrogen) grown under an atmosphere of 95% air and 5% $CO_2$ in DMEM supplemented with 10% fetal calf serum (FCS), 2 mM L-glutamine, 1000 U/ml penicillin, 1 mg/ml streptomycin and 5 µg/ml blasticidin. Other cell lines used are stably transfected derivatives of T-REx-293 that express the tetracycline repressor.

Different cell lines including PC12 and HeLa were also transfected with VDAC1 RNAi molecules.

hVDAC1-shRNA T-REx-293 cells: T-REx-293 cells, stably transfected with the pSUPERretro plasmid encoding shRNA targeting hVDAC1 were grown with 0.5 µg/ml puromycin and 5 µg/ml blasticidin.

pc-mVDAC1-hVDAC1-shRNA T-REx-293 cells: hVDAC1-shRNA-T-REx-293 cells were transfected with plasmid mVDAC1- or E72Q-mVDAC1-pcDNA4/TO, expressing mVDAC1 or E72Q-mVDAC1 under the control of tetracycline. Cells were grown with 200 µg/ml zeocin, 0.5 µg/ml puromycin and 5 µg/ml blasticidin.

Transfection and Selection of Stable Transformants

Cell transfection with plasmid pSUPERretro-shRNA-hVDAC1 by metafectene: $3 \times 10^5$ cells were cultured in a petri dish (60 mm) 24 h before transfection, cells were growing at 37° C. in a $CO_2$ incubator to 30-50% real confluency. For transfection two separate solutions were prepared: solution A—1 µg DNA in 50 µl medium free of serum and antibiotics; solution B—2.4 µl metafectene reagent in 50 µl medium free of serum and antibiotics, and then combined the two solutions, mixed gently by pipetting and incubated at room temperature for 20 min. after incubation discard cell medium and added 1 ml medium free serum and antibiotics and added the DNA lipid complexes to the cells and mix gently. After 5 hours 3 ml complete medium was added and continue growing the cells at 37° C. in a $CO_2$ incubator. Day after the transfection mixture was removed and replaced with 3 ml complete medium: DMEM supplemented with 10% FCS, 2 mM L-glutamine, 1000 U/ml penicillin, 1 mg/ml streptomycin and 5 µg/ml blasticidin, and continue growing the cells at 37° C. in a $CO_2$ incubator. The medium was then replaced, and 48 h later, 0.5 µg/ml puromycin was added for selection of transfected cells. Growth was monitored for two weeks with medium being refreshed every 48 h. Colonies were analyzed separately for hVDAC1 level by immunoblot using monoclonal anti-VDAC1 antibodies. A clone expressing about 10% of normal VDAC1 level was selected for further experiments.

Cell Transfection with Plasmid pcDNA4/TO Encoding Native or Mutated mVDAC1 by Lipofectamine or Metafectene.

Logarithmically-growing hVDAC1-shRNA-T-REx-293 cells were transfected with plasmid pcDNA4/TO-mVDAC1. Linearized NruI cut plasmid DNA was transfected into these cells as described above, and 48 h later, 200 µg/ml of zeocin was added for selection of transfected cells. After selection, transformed cells, referred to as mVDAC-hVDAC-shRNA-REx-293 cells, containing the two plasmids, i.e. pSUPERretro-expressing shRNA and pcDNA4/TO-mVDAC1 were obtained. The selected cells were grown with 200 µg/ml of zeocin, 0.5 µg/ml puromycin and 5 µg/ml blasticidin.

Tetracycline-induced mVDAC1 Expression

Induction of mVDAC1 expression in hVDAC1-shRNA-T-REx-293 cells was accomplished by exposing cells to 200-2500 ng/ml tetracycline. Cell growth rates were monitored using Trypan-Blue staining. The expression levels of mVDAC1 were followed by Western-blot analysis of cell extracts using monoclonal anti-VDAC1 antibodies and quantified by densitometry. As a control for protein amount in all samples, blotting with anti-actin antibodies was performed.

Acridine Orange/Ethidium Bromide Staining of Cells

Cell viability was analyzed by staining with acridine orange and ethidium bromide in PBS as described previously (Zaid et al, 2005). To record images, fluorescence microscopy (Olympus IX51) and an Olympus DP70 camera were used.

Light Microscope Immunocytochemistry

Cells cultured on cover slips in a 24-well dish were fixed using 4% paraformaldehyde and preincubated with a blocking solution containing 5% normal goat serum, 1% BSA and 0.2% Triton X-100 for 30 min, and then incubated with anti-VDAC1 antibodies diluted in blocking solution containing 1% normal goat serum for 2 h at room temperature. Following three washes with PBS, cells were incubated for 1 h with Alexa-488-conjugated antibody. Immunofluorescent signals were monitored using a Zeiss LSM 510 confocal microscope.

ATP Synthesis by Isolated Mitochondria

Mitochondria were isolated from control, hVDAC1-shRNA-T-REx-293 and hVDAC1-shRNA-T-REx-293 cells transfected to express mVDAC1 as described previously (Abu-Hamad, et al., 2006). ATP synthesis was assayed using an enzymatic assay coupled to NADP$^+$ reduction.

Citrate Synthase, ATP and ADP Levels

Citrate synthase activity was determined in cell extracts ($1 \times 10^7$ cells/ml) obtained by sonication using the coupled reaction among oxaloacetate, acetyl-CoA, and 5,5'-dithiobis (2,4-nitrobenzoic acid) as monitored at 412 nm (molar coefficient=14,150). ATP concentrations were determined by the luciferin/luciferase reaction. Cells ($3 \times 10^7$ cells/ml) were centrifuged, resuspended in PBS and perchloric acid was added to a final concentration of 6%. The mixture was centrifuged and the pellet was saved for protein determination. The neutralized supernatant was assayed for ATP and ADP levels. ADP was measured by converting ADP to ATP with 4 mM creatine phosphate and 5 units of creatine kinase.

Example 2

Suppression of VDAC1 Expression and Cell Proliferation by shRNA

RNA interference (RNAi) is a tool to control the expression of specific genes in numerous organisms. In one embodiment RNAi was performed using shRNA to interfere with the expression of endogenous VDAC1 in transformed primary human embryonal kidney T-REx-293 cells. Accordingly, a single shRNA targeting a coding region of human VDAC1 that differs in 3 nucleotides from the same region of murine VDAC1 was designed (Table 1).

Table 1. shRNA target nucleotide sequence in hVDAC1, and analogous sequences in mVDAC1 and in the hVDAC2 and hVDAC3 isoforms The nucleotides that differ from those in hVDAC1 are presented in bold and underlined letters. The numbers in each sequence indicate positions in the coding sequence.

| VDAC isoforms and species | Sequence |
|---|---|
| hVDAC1 | 159-AGTGACGGGCAGTCTGGAA-177 (SEQ ID NO:8) |
| mVDAC1 | 159-AGTGAACGGCAGCCTGGAA-177 (SEQ ID NO:14) |
| hVDAC2 | 192-AGTTACTGGACCTTGGAG-210 (SEQ ID NO:15) |
| hVDAC3 | 159-AGCATCAGGCAACCTAGAA-177 ((SEQ ID NO:16) |

Figure 1C:
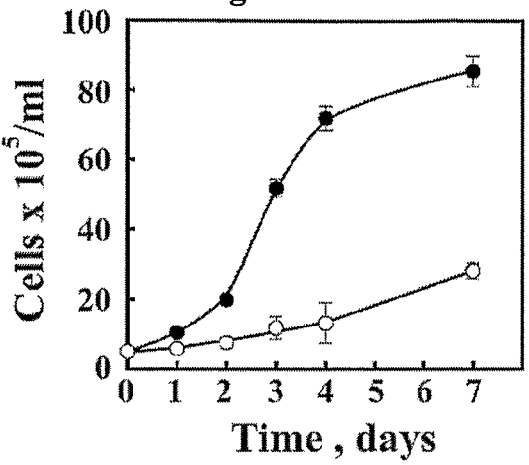
Figure 1B:
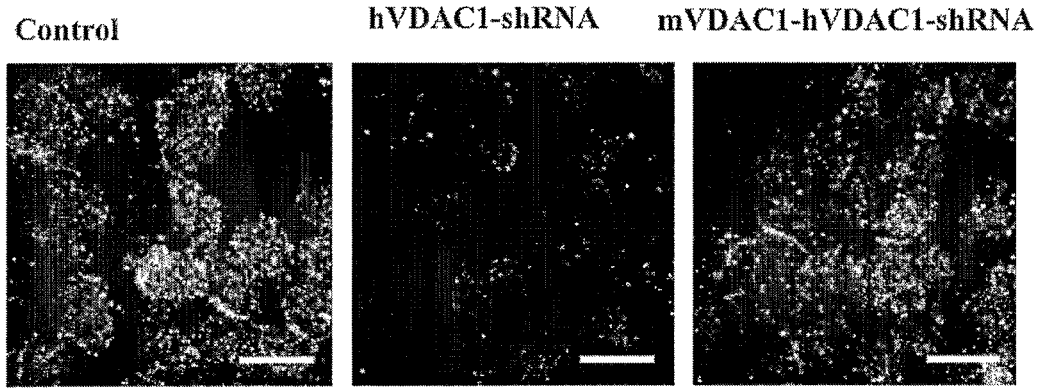

To determine the ability of this shRNA to limit VDAC1 expression in T-REx-293-cells expressing high levels of hVDAC1 was tested. Several stable clones of T-REx-293 cells transfected with a plasmid encoding hVDAC1-shRNA were analyzed by Western blotting using anti-VDAC1 antibodies. FIG. 1A. Immunoblot analyses of hVDAC1 and actin expression in control and various stable hVDAC1-shRNA-T-REx-293 colonies were performed, using anti-VDAC1 or anti-actin antibodies. FIG. 1B: Immunocytochemical analysis of VDAC1 expression in control, hVDAC1-shRNA-T-REx-293 and hVDAC1-shRNA-T-REx-293 expressing mVDAC1. Immunostaining using anti-VDAC1 antibodies and Alexa 488-conjugated anti-mouse antibodies as a secondary antibody and was monitored by confocal microscopy. Bar=20 μm. FIG. 1C: Quantitative analysis of cell growth rates of control and hVDAC1-shRNA-T-REx-293 cells followed by Trypan-Blue staining. The results represent the mean ±S.E.M of 4 different experiments carried out with different cells cultures.

Endogenous hVDAC1 expression was suppressed by 82-96% (FIG. 1A). Colony 1 was selected for further experiments. The dramatic decrease in VDAC1 expression is also clearly illustrated in representative confocal images of native and hVDAC1-shRNA-expressing cells immunostained with anti-VDAC1 antibody (FIG. 1B). The distribution of VDAC1 as visualized by confocal microscope was punctuate in control cells and hVDAC1-shRNA-T-REx cells expressing mVDAC1, suggesting that both native hVDAC1 and recombinant mVDAC1 were mostly localized to mitochondria.

The hVDAC1-shRNA-expressing cells showing a low level of VDAC1 expression proliferated extremely slowly in comparison to normal cells (FIG. 1C).

Decreased Cell Growth is Restored by Murine VDAC1

Next, it was verified whether the dramatically reduced cell growth observed upon RNAi is due to specific suppression of VDAC1 expression by the hVDAC1-shRNA used, rather than a result of interference with the expression of other proteins. As the shRNA sequence employed was designed to specifically inhibit the expression of human VDAC1 but not murine VDAC1 (see Table 1), the hVDAC1-shRNA-T-REx-293 cells were transfected to express mVDAC1 under the control of an inducible tetracycline-dependent human cytomegalovirus promoter (FIG. 2). FIGS. 2A-2E show murine VDAC1 (mVDAC1) expression in stably expressing shRNA-T-REx-293 cells restores cell growth. FIG. 2A: Growth of control cells (●), and hVDAC1-shRNA-T-REx-293 cells transfected with mVDAC1, grown without tetracycline (○), with 0.2 μg/ml (■) or (□) 1 μg/ml tetracycline, was monitored as a function of time. FIG. 2B: Cell growth of hVDAC1-shRNA-T-REx-293 cells transfected with mVDAC1 as a function of tetracycline concentration. Cell viability and growth rates were followed by Trypan-Blue staining. FIGS. 2C, 2D: The VDAC1 expression level on the sixth day of growth was analyzed in cells extracts (30 μg of protein) using anti-VDAC1 or anti-actin antibodies as a function of the indicated tetracycline concentration (2C) or as a function of time (2D). FIG. 2E: Quantitative analysis of immunoblots representing mVDAC1 expression level as a function of tetracycline concentration or of growth time and presented as percentage of the endogenous hVDAC1 in the control cells. The results represent the mean ±S.E.M of 4 to 7 different experiments carried out with different cells cultures.

Transfecting the T-REx-293 cells with a plasmid-based-tetracycline-inducible mVDAC1 expression system restored cell growth in a time- and tetracycline concentration-dependent manner (FIGS. 2A and 2B). Low tetracycline concentrations (below 1 μg/ml) promoted cell growth (FIGS. 2A and 2B) and mVDAC1 expression (FIGS. 2C and 2D). At the optimal tetracycline concentration (1 μg/ml), the growth rate of the cells ectopically expressing mVDAC1 was the same as that of the control T-REx-293 cells expressing native hVDAC1 (FIG. 2A). The decrease in cell growth observed at high concentrations of tetracycline was due to apoptotic cell death induced by mVDAC1 over-expression (see below).

The expression of murine VDAC1 in these cells is clearly shown in their immunostaining with anti-VDAC1 antibodies (FIG. 1B) and by Western blot. Analysis of the Western blots demonstrated that restoring cell growth was accompanied by progressive increase in the expression level of mVDAC1.

Moreover, an exponential relationship between cell growth restoration and increase in mVDAC1 expression was obtained (FIG. 2E), suggesting that cell growth required a certain minimal level of VDAC1.

Figure 3A:
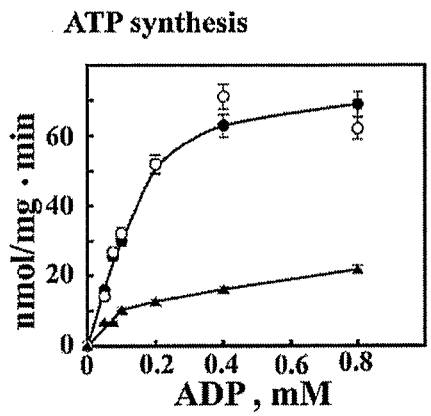
FIGS. 3A-3D show decreased cytosolic ATP levels and mitochondrial ATP synthesis rates in shRNA expressing cells, thereby representing a correlation between cell growth and ATP levels. Mitochondria were isolated from control, VDAC1-shRNA expressing cells and hVDAC1-shRNA expressing cells further expressing mVDAC1 induced by tetracycline.
Figure 3B:
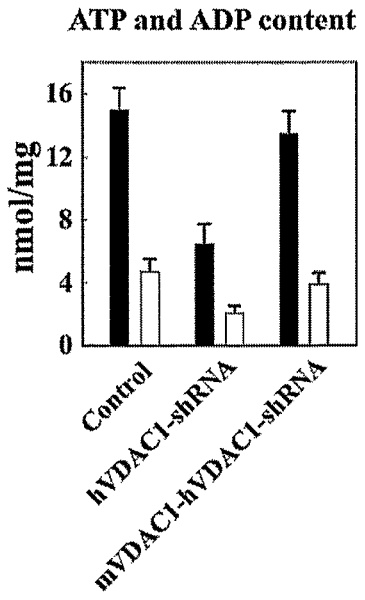
Figure 3C:
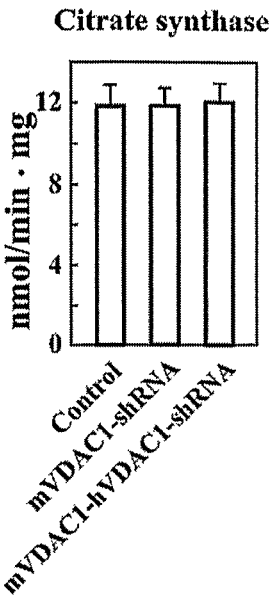
Figure 3D:
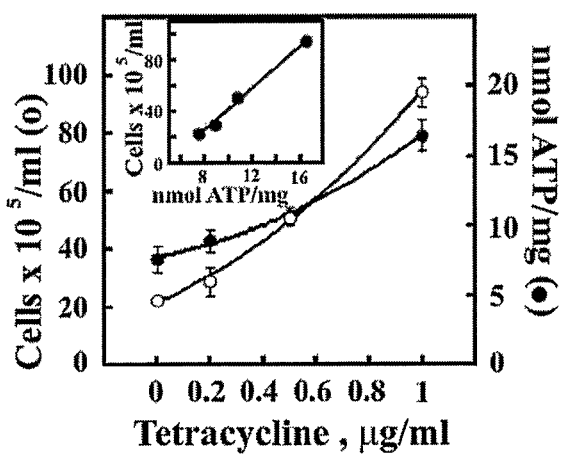

ATP Synthesis and Cellular Levels are Decreased in hVDAC1-shRNA-expressing Cells To ascertain that the down-expression of hVDAC1 leading to inhibition of cell proliferation acts through a disruption of energy production, rates of ATP synthesis by mitochondria isolated from either control, hVDAC1-shRNA-T-REx-293 cells and from the same cells expressing mVDAC1 were compared. FIGS. 3A-D show cytosolic ATP levels and mitochondrial ATP synthesis rates are decreased in shRNA-T-REx-293 cells—a correlation between cell growth and ATP levels. Mitochondria were isolated from control, VDAC1-shRNA-T-REx-293 and hVDAC1-shRNA-T-REx-293 cells expressing mVDAC1 induced by tetracycline (1 µg/ml). FIG. 3A: ATP synthesis by control (●), hVDAC1-shRNA-T-REx-293 (▲) and hVDAC1-shRNA-T-REx-293 cells expressing mVDAC1 (○), as a function of ADP concentration, was assayed as described (Abu-Hamad et al, 2006)). ATP (black) and ADP (grey) content, determined using luciferin/luciferase (FIG. 3B) and the citrate synthase activity (FIG. 3C) of cells extracts were assayed as described in (Abu-Hamad et al, 2006). ATP levels (●) and cell growth (○) were analyzed in hVDAC1-shRNA-T-REx-293 cells expressing mVDAC1 under the control of different concentrations of tetracycline (FIG. 3D). The inset shows the same results presented as cell growth as a function of the cellular ATP level. The results represent the mean ±S.E.M of 4 different experiments carried out with different mitochondrial preparations.

For all cell types, a half-maximal rate of ATP synthesis was obtained at about 100 µM ADP. However, the steady state level of ATP synthesis by mitochondria isolated from hVDAC1-shRNA-T-REx-293 cells was 4-fold lower than that of mitochondria isolated from control cells or from hVDAC1-shRNA cells transfected to also express mVDAC1 (FIG. 3A).

Since VDAC provides the major pathway for nucleotide movement across the outer mitochondrial membrane (OMM), the 4-fold decrease in the steady state level of ATP synthesized may be due to limited transport of ADP and/or synthesized ATP in and out of the mitochondria. Therefore, the next step was to measure the levels of ATP and ADP in control and hVDAC1-shRNAT-REx-293 cells (FIG. 3B). The results clearly showed a decrease of about 40% in the levels of ATP or ADP in the hVDAC1-shRNA T-REx-293 cells. The levels of ATP and ADP were, however, restored when the cells were transfected to express mVDAC1. Thus, the decrease in total ATP and ADP in the hVDAC1-shRNA-T-REx-293 cells may explain the slow growth of these cells.

To eliminate the possibility that decreased mitochondrial numbers was responsible for the observed decrease in ATP and ADP levels, the activity of citrate synthase, a marker of mitochondrial mass was assayed. No difference between control and hVDAC1-shRNA cells in the content of the mitochondrial matrix enzyme citrate synthase was observed (FIG. 3C).

The relationship between restoring cell growth due to mVDAC1 expression and ATP levels in the cells (FIG. 3D) clearly indicate a tight correlation between the two, and suggests that VDAC1 controls nucleotide fluxes into and out of the mitochondria.

Example 3

Inhibition of VDAC1 In Vivo

The ability of hVDAC1-shRNA to inhibit cancer cells prolifiration in animal model is analyzed by injecting subcutaneously T-REx-293 cells or hVDAC1-shRNA-T-REx-293 cells to nude mice, and tumor development is followed. Beginning 5-10 days later, tumor size is measured every 2 days. The tumor volume is calculated according to the formula: $V (mm3)=L●W2/2$ and at the end of the experiment the tumor will be weighted. The effects of encapsulated plasmid expressing hVDAC1-shRNA or synthetic RNAi on tumor proliferation will be tested. Plasmids are encapsulated into specially designed liposomes to allow specific delivery into the tumor tissue. Both plasmids and synthetic RNAi are administered intratumoraly so as to minimize leakiness and degradation of the preparations by plasma enzymes. The efficiency of cationic liposome-mediated systemic delivery of synthetic iRNAi molecules can be assessed using FITC-labeled hVDAC-shRNA and following its uptake by tissues from a group of mice receiving this RNAi molecule.

In a non-limiting example, the RNAi molecules are introduced into a mammalian cell by one of at least three ways:

via a mammalian expression vector that expresses the VDAC1 silencing molecule in an inducible or constitutive manner;

via liposomes or another encapsulating system;

via direct administration of a synthetic VDAC1 silencing molecule, which may be further chemically modified.

Discussion of Results

A VDAC1 expression silencing system has been established using, inter alia, a highly specific human VDAC1-shRNA. In this system, the level of hVDAC1 expression was dramatically decreased by 90%, indicating the effectiveness of the selected shRNA sequence. It should be noted that higher levels of suppression of VDAC1 expression were obtained, but due to a very slow cell growth, these cell lines were not selected for further study. Treated cells proliferated extremely slowly in comparison to normal hVDAC1-expressing cells, but normal growth rates were restored upon expression of mouse VDAC1. Again, indicating on the high specificity of the selected hVDAC1 sequence, differing in just three (3) nucleotides from the corresponding sequence in murine VDAC1. The results show that shRNA inhibited cell growth is directly related to the reduced or absent VDAC1 expression.

Without wishing to be bound to theory, it is possible that the decrease in energy production observed upon down regulation of VDAC1 expression is responsible for growth inhibition, as reflected in the strong relationship between growth and cellular ATP level (FIG. 3D). The decrease in ATP and ADP levels may reflect impaired translocation of ADP to the mitochondria and of the mitochondrially synthesized ATP to the cytosol, known to be mediated by VDAC located in the outer mitochondrial membrane.

The reduced growth, ATP synthesis rates and ATP and ADP content of the hVDAC1-shRNA-TREx 937 cells could be restored to normal rates by introducing mVDAC1 through an inducible expression vector. Over-expression of mVDAC1, however, initiated a mitochondrial death cascade in these cells. Such cell death, is not restricted to tetracycline-induced over-expression of mVDAC1 as the same phenomenon was observed in cell lines expressing mVDAC1-GFP, rat VDAC1 E72Q-mVDAC1 (Zaid, et al, 2005) or plant VDAC (Godbole et al, 2003).

In conclusion, upon shRNA silencing of VDAC1 expression, cell proliferation is attenuated. Without wishing to be bound to theory inhibition may be due to limited exchange of ATP/ADP and other metabolites between the cytosol and the mitochondrion, indicating that VDAC1 is necessary for normal cell growth. Thus, using hVDAC1-shRNA to interfere with VDAC1 expression constitutes a potential therapeutics for inhibiting cell growth. Recently, the therapeutic potential of siRNA has been recognized, particularly in areas of infectious diseases and cancer (Tong, et al, 2005, Ichim, et al, 2004). Silencing of Bcl-2 induced massive p53-dependent apoptosis (Jiang & Milner, 2003) and reducing the level of the androgen receptor in prostate cancer cells led to apoptosis by disrupting the Bcl-xL-mediated survival signal (Liao, et al, 2005).

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein.

REFERENCES

Ausubel et al., Short Protocols in Molecular Biology: A Compendium of Methods from Current Protocols in Molecular Biology, 5th Edition John Wiley & Sons Inc., 2002

Buettner R, Papoutsoglou G, Scemes E, Spray D C, Dermietzel R. (2000). Evidence for secretory pathway localization of a voltage-dependent anion channel isoform. *Proc Natl Acad Sci USA.* 28; 97(7):3201-6.

Czauderna F, Fechtner M, Dames S, Aygun H, Klippel A, Pronk G J, Giese K, Kaufmann J. (2003) Structural variations and stabilising modifications of synthetic siRNAs in mammalian cells. *Nucleic Acids Res.* (11):2705-16.

Colombini M. (2004). VDAC1: the channel at the interface between mitochondria and the cytosol. *Mol Cell Biochem.* 256-257: 107-15.

Fingl, et al., (1975). in "The Pharmacological Basis of Therapeutics", Ch. 1 p. 1

Gennaro (ed.), (2000) *Remington: The Science and Practice of Pharmacy,* 20th ed., Lippincott, Williams & Wilkins Godbole A, Varghese J, Sarin A, Mathew M K (2003). VDAC1 is a conserved element of death pathways in plant and animal systems. *Biochim. Biophys. Acta* 1642: 87-96.

Hammond S M. (2005) Dicing and slicing: the core machinery of the RNA interference pathway. *FEBS Lett.* 579 (26):5822-9.

Ichim, T. E., Li, M., Qian, H., Popov, I. A., Rycerz, K., Zheng, X., White, D., Zhong, R. & Min, W. P. (2004) RNA interference: a potent tool for gene-specific therapeutics. *Am J Transplant* 4, 1227-36.

Jiang, M and Milner, J (2003). Bcl-2 constitutively suppresses p53-dependent apoptosis in colorectal cancer cells. *Genes Dev* 17, 832-7.

Kumiko U, Yuki N, Fumitaka T, Takeshi H, Hiroko O-H, Aya J, Ryu U, Kaoru S. (2004). Guidelines for the selection of highly effective siRNA sequences for mammalian and chick RNA interference. *Nucl. Acids Res.* 32: 936-948

Khachigian L M (2002). DNAzymes: cutting a path to a new class of therapeutics. *Curr Opin Mol Ther* 4, 119-121.

Liao X, Tang S, Thrasher J B, Griebling T L, Li B (2005). Small-interfering RNA-induced androgen receptor silencing leads to apoptotic cell death in prostate cancer. Mol *Cancer Ther* 4, 505-15.

Milhavet O, Gary D S, Mattson M P. (2003). RNA interference in biology and medicine. *Pharmacol Rev.* 55(4):629-48.

Pillai O, Panchagnula R. (2001). Polymers in drug delivery, *Curr. Opin. Chem. Biol.* 5, 447-451.

Sambrook et al., Molecular Cloning: A Laboratory Manual, Cold Springs Harbor Laboratory, New York 1989, 1992;

Sapra P and Allen T M (2004). Improved outcome when B-cell lymphoma is treated with combinations of immunoliposomal anticancer drugs targeted to both the CD19 and CD20 epitopes. *Clin Cancer Res.* 10(7):2530-7.

Shoshan-Barmatz V and Gincel D (2003). The voltage-dependent anion channel: characterization, modulation, and role in mitochondrial function in cell life and death. *Cell Biochem Biophys* 39, 279-92.

Shoshan-Barmatz V, Israelson A, Bridiczka D, Sheu S S (2006). The Voltage-Dependent Anion Channel (VDAC1): Function in Intracellular Signalling, Cell Life and Cell Death. *Current Pharmaceutical design.* 12 (18): 2249-2270

Tong A W, Zhang Y A, Nemunaitis J (2005); Small interfering RNA for experimental cancer therapy. *Curr Opin Mol Ther* 7, 114-24.

Welch P J, Barber J R, Wong-Staal F. (1998). Expression of ribozymes in gene transfer systems to modulate target RNA levels. *Curr Opin Biotechnol* 9, 486-496).

Zaid H, Abu-Hamad S, Israelson A, Nathan, I, Shoshan-Barmatz V (2005). The voltage-dependent anion channel-1 modulates apoptotic cell death. *Cell Death Diff.* 12(7):751-60

---

The invention claimed:

1. An RNA interference (RNAi) molecule wherein the RNAi molecule comprises:
   a. a first ribo-oligonucleotide sequence having the nucleic acid sequence set forth in SEQ ID NO:6; and
   b. a second ribo-oligonucleotide sequence having the nucleic acid sequence set forth in SEQ ID NO:7;
   wherein said first ribo-oligonucleotide sequence and said second ribo-oligonucleotide sequence anneal to each other to form said RNAi molecule and wherein the RNAi molecule silences mitochondrial human voltage-dependent anion channel 1 (VDAC1) expression and the RNAi molecule inhibits T-REx-293 cell proliferation when an effective amount of said RNAi molecule is delivered to T-Rex-293 cell.

2. The RNAi molecule according to claim 1 having a sequence set forth in SEQ ID NO:10.

3. A polynucleotide construct comprising a DNA sequence expressing the RNAi molecule according to claim 1, wherein the DNA sequence comprises both SEQ ID NO:8 and SEQ ID NO:9 or comprises any one of SEQ ID NOs:11-13.

4. A host cell comprising the polynucleotide construct according to claim 3.

* * * * *

SEQUENCE LISTING

```
<160> NUMBER OF SEQ ID NOS: 16

<210> SEQ ID NO 1
<211> LENGTH: 283
<212> TYPE: PRT
<213> ORGANISM: HUMAN
<300> PUBLICATION INFORMATION:
<308> DATABASE ACCESSION NUMBER: NP_003365
<309> DATABASE ENTRY DATE: 2005-12-25
<313> RELEVANT RESIDUES IN SEQ ID NO: (1)..(283)

<400> SEQUENCE: 1

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30
```

```
Thr Lys Ser Glu Asn Gly Leu Glu Phe Thr Ser Ser Gly Ser Ala Asn
        35                  40                  45

Thr Glu Thr Thr Lys Val Thr Gly Ser Leu Glu Thr Lys Tyr Arg Trp
 50                  55                  60

Thr Glu Tyr Gly Leu Thr Phe Thr Glu Lys Trp Asn Thr Asp Asn Thr
 65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
               100                 105                 110

Lys Ile Lys Thr Gly Tyr Lys Arg Glu His Ile Asn Leu Gly Cys Asp
               115                 120                 125

Met Asp Phe Asp Ile Ala Gly Pro Ser Ile Arg Gly Ala Leu Val Leu
           130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
                180                 185                 190

Ser Ile Tyr Gln Lys Val Asn Lys Lys Leu Glu Thr Ala Val Asn Leu
            195                 200                 205

Ala Trp Thr Ala Gly Asn Ser Asn Thr Arg Phe Gly Ile Ala Ala Lys
210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
            275                 280

<210> SEQ ID NO 2
<211> LENGTH: 283
<212> TYPE: PRT
<213> ORGANISM: RAT
<300> PUBLICATION INFORMATION:
<308> DATABASE ACCESSION NUMBER: NP_112643
<309> DATABASE ENTRY DATE: 2005-10-17
<313> RELEVANT RESIDUES IN SEQ ID NO: (1)..(283)

<400> SEQUENCE: 2

Met Ala Val Pro Pro Thr Tyr Ala Asp Leu Gly Lys Ser Ala Arg Asp
 1               5                  10                  15

Val Phe Thr Lys Gly Tyr Gly Phe Gly Leu Ile Lys Leu Asp Leu Lys
                20                  25                  30

Thr Lys Ser Glu Asn Gly Leu Glu Phe Thr Ser Ser Gly Ser Ala Asn
        35                  40                  45

Thr Glu Thr Thr Lys Val Asn Gly Ser Leu Glu Thr Lys Tyr Arg Trp
 50                  55                  60

Thr Glu Tyr Gly Leu Thr Phe Thr Glu Lys Trp Asn Thr Asp Asn Thr
 65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
               100                 105                 110
```

```
Lys Ile Lys Thr Gly Tyr Lys Arg Glu His Ile Asn Leu Gly Cys Asp
            115                 120                 125

Val Asp Phe Asp Ile Ala Gly Pro Ser Ile Arg Gly Ala Leu Val Leu
130                 135                 140

Gly Tyr Glu Gly Trp Leu Ala Gly Tyr Gln Met Asn Phe Glu Thr Ser
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Leu Glu Thr Ala Val Asn Leu
        195                 200                 205

Ala Trp Thr Ala Gly Asn Ser Asn Thr Arg Phe Gly Ile Ala Ala Lys
        210                 215                 220

Tyr Gln Val Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 3
<211> LENGTH: 283
<212> TYPE: PRT
<213> ORGANISM: MOUSE
<300> PUBLICATION INFORMATION:
<308> DATABASE ACCESSION NUMBER: NP_035824
<309> DATABASE ENTRY DATE: 2005-12-11
<313> RELEVANT RESIDUES IN SEQ ID NO: (1)..(283)

<400> SEQUENCE: 3

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
                20                  25                  30

Thr Lys Ser Glu Asn Gly Leu Glu Phe Thr Ser Ser Gly Ser Ala Asn
            35                  40                  45

Thr Glu Thr Thr Lys Val Asn Gly Ser Leu Glu Thr Lys Tyr Arg Trp
50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Val Asp Phe Asp Ile Ala Gly Pro Ser Ile Arg Gly Ala Leu Val Leu
130                 135                 140

Gly Tyr Glu Gly Trp Leu Ala Gly Tyr Gln Met Asn Phe Glu Thr Ser
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
```

|   |   |   |   |   | 180 |   |   |   |   | 185 |   |   |   |   | 190 |   |   |
|---|---|---|---|---|-----|---|---|---|---|-----|---|---|---|---|-----|---|---|

Ser Ile Tyr Gln Lys Val Asn Lys Lys Leu Glu Thr Ala Val Asn Leu
    195                 200                 205

Ala Trp Thr Ala Gly Asn Ser Asn Thr Arg Phe Gly Ile Ala Ala Lys
210                 215                 220

Tyr Gln Val Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
    275                 280

<210> SEQ ID NO 4
<211> LENGTH: 1806
<212> TYPE: RNA
<213> ORGANISM: HUMAN
<300> PUBLICATION INFORMATION:
<308> DATABASE ACCESSION NUMBER: NP_003374
<309> DATABASE ENTRY DATE: 2006-08-20
<313> RELEVANT RESIDUES IN SEQ ID NO: (1)..(1806)

<400> SEQUENCE: 4

| | | |
|---|---|---|
| gccgcucgcu cggcuccgcu cccuggcucg gcucccugcc uccgcgucgc agccccgcc | 60 |
| guagccgccu ccgagcccgc cgccacaucc ucugagaaga uggcugugcc acccacguau | 120 |
| gccgaucuug gcaaaucugc cagggauguc uucaccaagg gcuauggauu uggcuuaaua | 180 |
| aagcuugauu ugaaaacaaa aucugagaau ggauuggaau uuacaagcuc aggcucagcc | 240 |
| aacacugaga ccaccaaagu gacgggcagu cuggaaacca guacagaugg acugaguac | 300 |
| ggccugacgu uuacagagaa augggauacc gacaauacac uaggcaccga gauuacugug | 360 |
| gaagaucagc uugcacgugg acugaagcug accuucgauu caucuucuc accuaacacu | 420 |
| gggaaaaaaa augcuaaaau caagacaggg uacaagcggg agcacauuaa ccugggcugc | 480 |
| gacauggauu ucgacauugc ugggccuucc auccggggug cucuggugcu agguuacgag | 540 |
| ggcuggcugg ccggcuacca gaugaauuuu gagacugcaa aucccgagu gacccagagc | 600 |
| aacuuugcag uuggcuacaa gacugaugaa uccagcuuc acacuaaaugu gaaugacggg | 660 |
| acagaguuug gcggcuccau uuaccagaaa gugaacaaga guuggagac gcugucaau | 720 |
| cuugccugga cagcaggaaa caguaacacg cgcuucggaa uagcagccaa guacagauu | 780 |
| gacccugacg ccugcuucuc ggcuaaagug aacaaucuca gccugauagg uuuaggauac | 840 |
| acucagacuc uaaagccagg uauuaaacug acacugucag cucuucgga uggcaagaac | 900 |
| gucaaugcug guggccacaa gcuuggucua ggacuggaau ucaagcaua aaugaauacu | 960 |
| guacaauugu uuaauuuaa acuauuuugc agcauagcua ccuucagaau uuagugauc | 1020 |
| uuuuaauguu guaugucugg gaugcaagua uugcuaaaua uguuagcccu ccagguuaaa | 1080 |
| guugauucag cuuuaagaug uuacccuucc agagguacag aagaaaccua uuccaaaaa | 1140 |
| agguccuuuc agugguagac ucggggagaa cuugguggcc ccuuugagau gccagguuuc | 1200 |
| uuuuuuaucu agaaauggcu gcaaguggaa gcggauaaua uguaggcacu uguaaauuc | 1260 |
| auauugagua aaugaaugaa auugugauuu ccugagaauc gaaccuuggu ucccuaacc | 1320 |
| uaauugauga gaggcucgcu gcuugauggu guguacaaac ucaccugaau gggacuuuu | 1380 |
| uagacagauc uucaugaccu guucccaccc caguucauca ucaucucuuu uacaccaaaa | 1440 |

```
ggucugcagg gugugguaac uguuucuuuu gugccauuuu gggguggaga agguggaugu    1500
gaugaagcca auaauucagg acuuauuccu ucuuguguug uguuuuuuuu uggcccuugc    1560
accagaguau gaaauagcuu ccaggagcuc cagcuauaag cuuggaagug ucugugugau    1620
uguaaucaca uggugacaac acucagaauc uaaauuggac uucuguugua uucucaccac    1680
ucaauuuguu uuuuagcagu uuaaugggua cauuuuagag ucuuccauuu guuggaauu    1740 agauccuccc cuucaaaugc uguaauuaac aacacuuaaa aaacuugaau aaaauauuga    1800
aaccuc                                                              1806
```

```
<210> SEQ ID NO 5
<211> LENGTH: 852
<212> TYPE: DNA
<213> ORGANISM: HUMAN
<300> PUBLICATION INFORMATION:
<308> DATABASE ACCESSION NUMBER: NM_003374
<309> DATABASE ENTRY DATE: 2005-12-25
<313> RELEVANT RESIDUES IN SEQ ID NO: (1)..(852)

<400> SEQUENCE: 5
atggctgtgc cacccacgta tgccgatctt ggcaaatctg ccaggatgt cttcaccaag      60 ggctatggat ttggcttaat aaagcttgat ttgaaaacaa atctgagaa tggattggaa     120 tttacaagct caggctcagc caacactgag accaccaaag tgacgggcag tctggaaacc    180
aagtacagat ggactgagta cggcctgacg tttacagaga atggaatac cgacaataca    240 ctaggcaccg agattactgt ggaagatcag cttgcacgtg gactgaagct gaccttcgat    300
tcatccttct cacctaacac tgggaaaaaa aatgctaaaa tcaagacagg gtacaagcgg    360
gagcacatta acctgggctg cgacatggat ttcgacattg ctgggccttc catccggggt    420
gctctggtgc taggttacga gggctggctg gccggctacc agatgaattt tgagactgca    480
aaatcccgag tgacccagag caactttgca gttggctaca gactgatga attccagctt    540 cacactaatg tgaatgacgg gacagagttt ggcggctcca tttaccagaa agtgaacaag    600
aagttggaga ccgctgtcaa tcttgcctgg acagcaggaa acagtaacac gcgcttcgga    660
atagcagcca agtatcagat tgaccctgac gcctgcttct cggctaaagt gaacaactcc    720
agcctgatag gtttaggata cactcagact ctaaagccag gtattaaact gacactgtca    780
gctcttctgg atggcaagaa cgtcaatgct ggtggccaca gcttggtctc aggactggaa    840
tttcaagcat aa                                                       852
```

```
<210> SEQ ID NO 6
<211> LENGTH: 19
<212> TYPE: RNA
<213> ORGANISM: ARTIFICIAL
<220> FEATURE:
<223> OTHER INFORMATION: ribo-oligonucleotide
<220> FEATURE:
<221> NAME/KEY: misc_feature
<222> LOCATION: (1)..(19)
<223> OTHER INFORMATION: SEQUENCE FROM mRNA OF NM_003374 BASES 158-176

<400> SEQUENCE: 6
agugacgggc agucuggaa                                                  19
```

```
<210> SEQ ID NO 7
<211> LENGTH: 19
<212> TYPE: RNA
<213> ORGANISM: ARTIFICIAL
<220> FEATURE:
<223> OTHER INFORMATION: ribo-oligonucleotide sequence complementary to
      SEQ ID NO:6
```

```
<400> SEQUENCE: 7
uuccagacug cccgucacu                                               19

<210> SEQ ID NO 8
<211> LENGTH: 19
<212> TYPE: DNA
<213> ORGANISM: ARTIFICIAL
<220> FEATURE:
<223> OTHER INFORMATION: oligonucleotide

<400> SEQUENCE: 8
agtgacgggc agtctggaa                                               19

<210> SEQ ID NO 9
<211> LENGTH: 19
<212> TYPE: DNA
<213> ORGANISM: ARTIFICIAL
<220> FEATURE:
<223> OTHER INFORMATION: oligonucleotide complentary to SEQ ID No:8

<400> SEQUENCE: 9
ttccagactg cccgtcact                                               19

<210> SEQ ID NO 10
<211> LENGTH: 56
<212> TYPE: RNA
<213> ORGANISM: ARTIFICIAL
<220> FEATURE:
<223> OTHER INFORMATION: ribo-oligonucleotide

<400> SEQUENCE: 10
cccagugacg ggcagucugg aauucaagag auuccagacu gcccgucacu uuuuua      56

<210> SEQ ID NO 11
<211> LENGTH: 56
<212> TYPE: DNA
<213> ORGANISM: ARTIFICIAL
<220> FEATURE:
<223> OTHER INFORMATION: oligonucleotide complementray to SEQ ID NO:10.

<400> SEQUENCE: 11
gggtcactgc ccgtcagacc ttaagttctc taaggtctga cgggcagtga aaaaat      56

<210> SEQ ID NO 12
<211> LENGTH: 60
<212> TYPE: DNA
<213> ORGANISM: ARTIFICIAL
<220> FEATURE:
<223> OTHER INFORMATION: oligonucleotide

<400> SEQUENCE: 12
gatccccagt gacgggcagt ctggaattca agagattcca gactgcccgt cacttttta   60

<210> SEQ ID NO 13
<211> LENGTH: 60
<212> TYPE: DNA
<213> ORGANISM: ARTIFICIAL
<220> FEATURE:
<223> OTHER INFORMATION: oligonucleotide

<400> SEQUENCE: 13
gggtcactgc ccgtcagacc ttaagttctc taaggtctga cgggcagtga aaaaattcga  60

<210> SEQ ID NO 14
<211> LENGTH: 19
```

```
-continued

<212> TYPE: DNA
<213> ORGANISM: MURINE

<400> SEQUENCE: 14
agtgaacggc agcctggaa                                              19

<210> SEQ ID NO 15
<211> LENGTH: 19
<212> TYPE: DNA
<213> ORGANISM: HUMAN

<400> SEQUENCE: 15
agttactggg accttggag                                              19

<210> SEQ ID NO 16
<211> LENGTH: 19
<212> TYPE: DNA
<213> ORGANISM: HUMAN

<400> SEQUENCE: 16
agcatcaggc aacctagaa                                              19
```